(12) United States Patent
Malessa et al.

(10) Patent No.: US 9,327,033 B2
(45) Date of Patent: May 3, 2016

(54) DEGRADATION-STABILISED, BIOCOMPATIBLE COLLAGEN MATRICES

(71) Applicant: MedSkin Solutions Dr. Suwelack AG, Billerbeck (DE)

(72) Inventors: Ralf Malessa, Essen (DE); Anja Kassner, Münster (DE)

(73) Assignee: MEDSKIN SOLUTIONS DR. SUWELACK AG, Billerbeck (DE)

( * ) Notice: Subject to any disclaimer, the term of this patent is extended or adjusted under 35 U.S.C. 154(b) by 0 days.

(21) Appl. No.: 14/228,285

(22) Filed: Mar. 28, 2014

(65) Prior Publication Data

US 2014/0287006 A1    Sep. 25, 2014

Related U.S. Application Data

(62) Division of application No. 13/329,477, filed on Dec. 19, 2011, now Pat. No. 8,722,854.

(30) Foreign Application Priority Data

Dec. 23, 2010    (EP) .................................... 10196934

(51) Int. Cl.

| | | |
|---|---|---|
| *A61K 47/42* | (2006.01) | |
| *A61K 8/02* | (2006.01) | |
| *A61K 8/65* | (2006.01) | |
| *A61L 15/32* | (2006.01) | |
| *A61L 27/24* | (2006.01) | |
| *A61Q 19/00* | (2006.01) | |
| *A61K 8/37* | (2006.01) | |
| *A61K 9/70* | (2006.01) | |
| *A61K 38/39* | (2006.01) | |
| *A61K 45/06* | (2006.01) | |
| *A61Q 19/02* | (2006.01) | |

(52) U.S. Cl.
CPC ................ *A61K 47/42* (2013.01); *A61K 8/0204* (2013.01); *A61K 8/0212* (2013.01); *A61K 8/37* (2013.01); *A61K 8/65* (2013.01); *A61K 9/70* (2013.01); *A61K 38/39* (2013.01); *A61K 45/06* (2013.01); *A61L 15/32* (2013.01); *A61L 27/24* (2013.01); *A61Q 19/00* (2013.01); *A61Q 19/007* (2013.01); *A61Q 19/02* (2013.01)

(58) Field of Classification Search
None
See application file for complete search history.

(56) References Cited

U.S. PATENT DOCUMENTS 6,117,979 A    9/2000    Hendriks et al.

FOREIGN PATENT DOCUMENTS

| DE | 10350654 A1 | 6/2005 |
|---|---|---|
| WO | 03/053490 A1 | 7/2003 |

OTHER PUBLICATIONS

Machine translation of DE 10350654 published Jun. 2, 2005, 38 pages.

*Primary Examiner* — Suzanne M Noakes
(74) *Attorney, Agent, or Firm* — Ballard Spahr LLP

(57) ABSTRACT

The present invention relates to degradation-stabilized, biocompatible collagen matrices which are distinguished in particular by the fact that they contain soluble collagen and peptide constituents, to processes for the preparation of such collagen matrices, which processes include in particular chemical crosslinking with an epoxy-functional crosslinking agent, and to the use of the collagen matrices according to the invention as a cosmetic or pharmaceutical agent, in particular for topical use, and as a wound treatment agent, as an implant or as a haemostatic agent in humans or animals, and as a scaffold for cell population in the biotechnology, basic research and tissue engineering field.

13 Claims, 5 Drawing Sheets

DEGRADATION-STABILISED, BIOCOMPATIBLE COLLAGEN MATRICES

INTRODUCTION AND PRIOR ART

Figure 1:
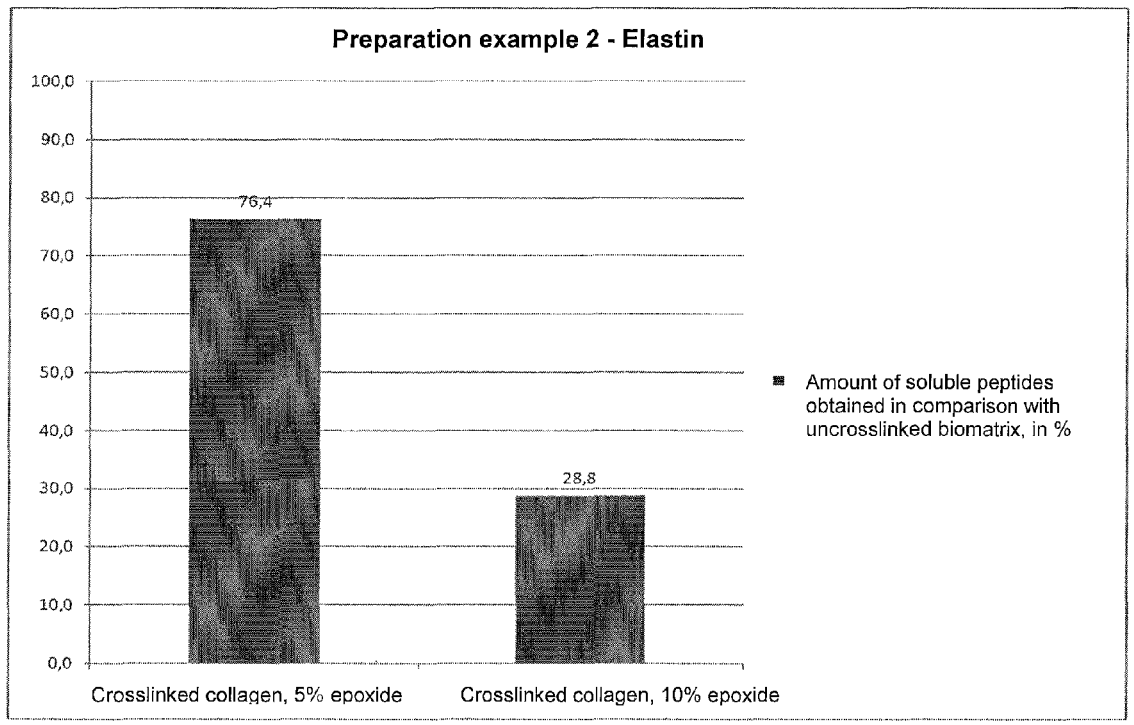

The present invention relates to degradation-stabilised, biocompatible collagen matrices which are distinguished in particular by the fact that besides unsoluble collagen fibers they contain soluble collagen and peptide constituents, to processes for the preparation of such collagen matrices, which processes include in particular chemical crosslinking with an epoxy-functional crosslinking agent, and to the use of the collagen matrices according to the invention as a cosmetic or pharmaceutical agent, in particular for topical use, and also as a wound treatment agent, as an implant or as a haemostatic agent in humans or animals, and as a scaffold for cell population in the biotechnology, basic research and tissue engineering field.

In the field of collagen materials, the provision of materials and scaffolds which are mechanically stable, flexible and show adequate stability against biological degradation plays an important role. Such product requirements are becoming increasingly important in particular in the field of wound treatment, biological implants and in the field of tissue engineering and the cell population of scaffolds, but also in the field of high-sorptive materials in the field of wound healing and haemostasis. In the cosmetic field, it is additionally desirable in particular for materials to have a pleasant feel and appearance while at the same time being well tolerated by the skin. Furthermore, the provision of active ingredients via such degradation-stabilised support or base materials, which additionally have high mechanical stability, is an important aspect in both cosmetic and pharmaceutical applications and in tissue engineering. The combination, for example, of scaffolds of tissue engineering with active ingredients is a strategy which is reflected in a large number of publications. Active ingredients which develop their biological activity over a prolonged period by being adsorptively or covalently bonded to the scaffold or released continuously from a depot belong to the prior art. Continuous release from a corresponding active ingredient depot opens up targeted interventions in wound healing in particular in the case of active ingredients which have a short biological half-life. For example, many critical phenomena, for example cell differentiation, cell proliferation and aggregation, are influenced by signal proteins via gene expression. The availability and differentiation, the regeneration or the replacement of individual cells, cell division and regulation are the main aims of research (Rui Miguel Paz, Dissertation RWTH Aachen 2004). Equipping biomaterials with biologically active substances in order to improve their functionality illustrates the development of the purely passive implant material into an active implant which enters into purposive interaction with the surrounding tissue or the tissue fluid. Combinations of biologically active substances with biomaterials are widespread in medicine and play an increasing role, for example in the prevention of implant-related infections. For example, in the field of wound dressings, an increasingly more important role is played by an improved wound environment, the reduction of infections and the stimulation of cell growth by adding active ingredients but also by purposively influencing cell differentiation and the expression pattern of the cells by adjusting the physical properties of the material, such as in particular the rigidity of the matrix material, in a controllable manner. So-called wound exudate management, which in the case of chronic wounds in particular concerns the influence and interaction especially in exuding, i.e. weeping, wounds both at physical level, via purely adsorptive functions, management of the wound exudate, etc., and at pharmacological level, release of active ingredients, has also become more important in recent years.

The loading of collagen matrices with protein active ingredients, such as growth factors, has been known for a long time and is described, for example, in WO 85/04413 or in U.S. Pat. No. 5,219,576 (EP 0428541 B1).

However, in order also to be able to achieve the product requirements of high mechanical stability of the support materials, and also to achieve a reduction in excessively rapid biological degradation, which is undesirable, for example in a wound or in implants in the body, the method of crosslinking, in particular crosslinking with chemical crosslinking agents, is known and widespread. In particular, it is also known to carry out chemical crosslinking of collagen with epoxy-functional crosslinking agents.

In this connection there are predominantly known processes in which crosslinking with the epoxy crosslinker is carried out on a solid, dry, generally freeze-dried collagen material. DE 69533285, for example, describes meniscus prostheses of biopolymer fibres which can be chemically crosslinked or partially crosslinked, the crosslinking taking place on the already freeze-dried collagen fibres.

WO 2003/053490 A1 (EP 1455855 A1) also provides freeze-dried collagen materials which can be chemically crosslinked. The chemical crosslinking of freeze-dried collagen-elastin materials is also described here, glutaraldehyde being used as the chemical crosslinking agent and epoxides being mentioned only generally as crosslinking agents.

DE 102006006461 A1 and DE 102004039537 A1 provide collagen matrices populated with skin cells (full skin model), wherein the populated collagen materials are subjected to chemical crosslinking with glutaraldehyde. A large number of further chemical crosslinking agents are listed only generally. Here too, only crosslinking of the already freeze-dried materials is described.

Chemical crosslinking in these processes is conventionally carried out by immersing the solid collagen materials, in particular those in the form of sheets or layers, in a solution containing the crosslinking agent. The sheet-like solid collagen materials (layer) are generally first obtained by drying (e.g. freeze-drying) collagen materials by conventional processes and, after being immersed in a solution containing the crosslinking agent, are subjected to a further drying step (e.g. further freeze-drying). In an additional step, after the crosslinking reaction has taken place, excess crosslinking agent that has not been coupled is generally washed out of the material by intensive rinsing, which is necessary in view of the biocompatibility of the crosslinked material or the reduction in its toxicity caused by crosslinking agent residues.

A corresponding process is described in particular in "Cross-linking of Collagen-based materials" (dissertation R. Zeeman, 1998) and by Zeeman et al. in J Biomed Mater Res, 46, 424-433, 1999, in J Biomed Mater Res, 47, 270-277, 1999, in Biomaterials, 20, 921-931, 1999, and in J Biomed Mater Res, 51, 541-548, 2000. In that process, for example, layered dermal sheep collagen (DSC layer) obtained by freeze-drying is immersed at acid or alkaline pH in a solution of an epoxy-functional crosslinking agent such as 1,4-butanediol diglycidyl ether (BDDGE) and crosslinked over a period of several days at room temperature (20-30° C.). The fully crosslinked collagen layers are then washed and freeze-dried again in order to obtain the epoxy-crosslinked collagen materials. In those publications, it is described that the pH value used for the crosslinking has a significant influence on the flexibility and elasticity of the crosslinked material, materials crosslinked at an acid pH value <6 (pH 4-6) having a higher flexibility and elasticity as compared with materials crosslinked at an alkaline pH value.

EP 0898973 B1 also describes a process for the chemical crosslinking of collagen. A collagen suspension is also mentioned in principle herein as a possible starting material for the chemical crosslinking. However, the described crosslinking process consists substantially of at least two crosslinking steps and is generally carried out at pH values of 4-9. The only concrete implementation example, wherein crosslinking is carried out with epoxide crosslinkers such as BDDGE, relates to sheet-form dermal sheep collagen (DSC) as described above, which is immersed in a solution containing BDDGE and, after a reaction time of 7 days, washed and then freeze-dried again.

Disadvantages of such processes, wherein crosslinking is carried out by immersing a solid, dried (freeze-dried) collagen material and then drying it again, are on the one hand the necessity of carrying out several drying steps, which is disadvantageous in particular for reasons of process economy, and on the other hand the high outlay in terms of time associated in particular with the crosslinking times, which extend over several days. It is also found that, when a crosslinked, already freeze-dried material is freeze-dried again, an undesirable change in the material, in particular in the form of shrinkage of the layered material, can be observed. Disadvantageous effects on the structure of the collagen material, for example increased denaturing or other structural changes in the collagen peptide structure, in particular in collagen materials in which the collagen is present as the native, biological structural protein, are additionally to be expected due to the increased thermal stress on the collagen material which is inevitably caused by the additional second drying process.

By contrast, there is known from EP 0793511 A1, for example, a process for the production of composite biopolymer foams, comprising inter alia also polymer mixtures of collagen and elastin, wherein the crosslinking agent is added to a polymer suspension and only then is a single drying step, in particular freeze-drying, carried out. Crosslinking of such polymer mixtures with epoxy-functional crosslinkers is not disclosed, however.

EP 0680990 A1 also describes the addition of the crosslinking agent to a polymer suspension, polymer mixtures of collagen and a synthetic hydrophilic polymer such as in particular a functionally activated synthetic hydrophilic polymer such as, for example, a glycol, preferably a difunctionally activated polyethylene glycol (PEG), being subjected to the crosslinking reaction. Epoxide as crosslinking agent is listed only generally as one of many possible crosslinking agents.

U.S. Pat. No. 4,883,864 describes chemically modified (crosslinked) collagen compositions, wherein the collagen is solubilised by means of pepsin and is then crosslinked by addition of the crosslinking agent. Epoxide is likewise mentioned in this publication merely generally as a possible crosslinking agent. Example 18 mentions that the collagen materials according to the invention can be freeze-dried and used as surgical sponge material. The use of insoluble native collagen or the concrete use of epoxide, in particular in connection with the freeze-drying step, is also not disclosed herein.

Chemically crosslinked collagen materials, in particular those of acid-insoluble native collagen, are already known from DE 10350654 A1, an older patent application of the applicant. In that application, aqueous collagen suspensions having a pH value of 2-4 are preferably used. In addition, the possibility of adding crosslinking agents to such aqueous collagen suspensions and subsequently freeze-drying is mentioned. It is further mentioned that, in particular when using crosslinking agents that react in an acid medium, the crosslinking treatment can take place before the freeze-drying. Various groups of polyfunctional crosslinking agents are listed as possible crosslinking agents, this general list also including diepoxides such as 1,4-butanediol diglycidyl ether (BDDGE). A dehydrothermal crosslinking is preferably carried out, however. For materials crosslinked by means of EDC (1-ethyl-3-(3-dimethylaminopropyl)carbodiimide), the surprising improvement in the angiogenetic properties of the collagen material is also mentioned. In connection with the dehydrothermal crosslinking which is distinguished therein as being preferred, freeze-drying temperatures of at least 50 to 180° C. are mentioned, higher temperatures above 80° C. being distinguished as preferred for the dehydrothermal crosslinking. A concrete choice of epoxides as crosslinking agents, in particular in combination with a concrete procedure which takes account of, for example, a concrete pH value <4 and a chosen freeze-drying temperature range, is not evident therefrom. Moreover, this document describes the working-up and preparation of a collagen suspension of fibrous, native insoluble collagen. There are, however, no references to the preservation of releasable acid-soluble collagen and peptide constituents, which are presumably formed within the context of this working-up, in the collagen material. In particular in connection with chemical crosslinking, which is mentioned only generally, neither the necessity of preserving such soluble constituents nor a possibility therefore is mentioned. By contrast, this document refers explicitly to the desired use of acid-insoluble collagen material, and acid-soluble collagen is referred to explicitly as being disadvantageous. The introduction of, for example, proteinogenic active ingredients (growth factors etc.) is achieved herein by encapsulation and incorporation of microspheres.

Native acid-insoluble collagen conventionally refers to the fraction of a collagen suspension that is insoluble in acid solution, can be precipitated by centrifugation and contains fibres visible by light microscopy; within the scope of the present invention, native acid-insoluble collagen includes in particular the fraction of a pure collagen suspension that is insoluble in an acid solution of pH <4, can be precipitated by centrifugation at 16,000 g and contains fibres which are visible under a light microscope (fibre thickness 0.2 µm and above).

Native soluble, or acid-soluble, collagen, on the other hand, denotes the collagen fraction that forms a clear solution in acid solution at pH <4 and does not contain any fibre structures which are visible under a light microscope.

Native soluble, or acid-soluble, collagen can be separated by means of fractionation, for example by means of known processes of SEC (size exclusion chromatography), into higher molecular weight, native, complete collagen molecules having a molecular weight >250 kDa and low molecular weight collagen peptides having a molecular weight <250 kDa. The low molecular weight collagen peptides can thereby not be assigned to a complete collagen molecule.

In principle, the presence of soluble complete collagen molecules as well as of low molecular weight peptide constituents can be detected qualitatively by analysis of the soluble constituents by means of known methods, for example SDS-PAGE (sodium dodecyl sulfate-polyacrylamide gel electrophoresis), as described in the following examples.

The acid-soluble collagen constituents and collagen peptides have various advantageous characteristics. For example, they have film-forming properties and, when applied topically or released from a carrier material on the skin, they can improve the water-retention capacity of the skin, and accordingly reduce the transepidermal water loss, via that film formation. Furthermore, soluble collagen fragments are important signal messengers and matrix constituents which bring about positive properties in the treatment of wounds and in the controllability of cell population/cell reaction, which is advantageous and desirable in particular in the field of tissue engineering with regard to the so-called expression profile of cell populations. An important aspect of the present invention is, therefore, to preserve such acid-soluble collagen constituents and peptides as well as other low molecular weight peptide constituents in the freeze-dried, degradation-stabilised (chemically crosslinked) collagen matrix so that, when used, they are released from the matrix and are able to achieve their advantageous action at the site of application.

The chemically crosslinked and thereby degradation-stabilised collagen materials known from the prior art no longer contain the acid-soluble collagen fractions, fragments and other peptide constituents, either because of the fundamental nature of the material, for example in the case of split-skin collagen or the above-described dermal sheep collagen (DSC) layers, or because of the epoxide crosslinking process which is carried out and the crosslinking conditions applied therein. The epoxy crosslinking processes described in the prior art are carried out using a marked excess of crosslinking agent in a high amount by volume of solvent over a long period of at least 72 hours. The soluble fractions which may be present in the raw material are thereby liberated by the large amount of solvent, diluted and accordingly washed out. As a result of the high diluting effect, soluble peptide and collagen fractions are still present in the material in only small amounts. The soluble peptide and collagen constituents still present to small degrees are crosslinked with the collagen strands by the high crosslinking agent concentrations and the long crosslinking times and are accordingly inseparably bonded in the crosslinked material. Because the described processes additionally include as a necessary step the washing out of the crosslinking agent from the crosslinked material, any non-bonded soluble collagen fractions or soluble collagen fragments or low molecular weight soluble peptide constituents are washed out of the crosslinked material in that washing step at the latest. Accordingly, the prior art does not provide chemically crosslinked collagen materials which, as well as having high degradation stability and mechanical strength as a result of the chemical crosslinking, at the same time have high biocompatibility (low toxicity) and acid-soluble collagen fractions, fragments and/or other peptide constituents which can be released from the crosslinked material.

OBJECT

The object of the present invention was, therefore, to provide freeze-dried collagen matrices which have both high biological degradation stability (hydrolytic stability) and a mechanical tear strength suitable for cosmetic and medical applications, in particular in the hydrated state (wet tear strength). In addition, the collagen matrices are to have high biocompatibility, characterised by low toxicity, and are to permit the release of soluble collagen and peptide constituents from the crosslinked matrix on use. In addition, the crosslinked collagen matrices are to have a high liquid absorption capacity and hydration rate, and the collagen matrices are to have high flexibility and elasticity as well as being pleasant to the touch and having attractive optical properties (e.g. high optical density), in order to be suitable in particular as cosmetic or pharmaceutical agents, especially for use as cosmetic dressings or masks and as wound treatment agents, implants or haemostatic agents and also as scaffolds for cell population/cell cultivation in tissue engineering. In a further aspect, collagen matrices are to be provided which, as a result of a controlled adaptation of the rigidity, allow cell differentiation and the expression pattern of the cells to be influenced purposively in the biotechnology, basic research and tissue engineering field. A scaffold which is stable and optimised in respect of the influencing of the expression pattern of cells, and high biocompatibility of the collagen material, are requirements for the facilitated incorporation of new cells and their performance, for example when used as an implant and when used as a cell scaffold in tissue engineering.

Last but not least, the process is to be superior to the prior art from an economic point of view.

DESCRIPTION OF THE INVENTION

The inventors found that such a specific, improved collagen material can be obtained by adding, at a pH value <4, an epoxy-functional crosslinking agent to an aqueous suspension of collagen comprising, in addition to fibrous, acid-insoluble native collagen, also fractions of native-soluble (acid-soluble) collagen and collagen peptides, as defined hereinbefore, and/or structure-forming agents and active ingredients from the group of the matrix proteins, extracellular matrix constituents, proteinogenic active ingredients and soluble protein or peptide constituents, and then freezing this mixture and freeze-drying it at a temperature <100° C. In particular it has been shown, surprisingly, that this novel process enabled the content of epoxide crosslinking agent to be drastically reduced as compared with crosslinker contents known from the prior art without obtaining losses in terms of the degree of crosslinking. A low pH value <4 as well as reduced crosslinking agent contents are advantageous in particular in respect of the residual epoxide activity after freeze-drying and in respect of the preservation of the uncrosslinked soluble collagen and peptide constituents which can be released on use, and accordingly in respect of the toxicity and biocompatibility of the crosslinked collagen material. Lower freeze-drying temperatures than those conventionally applied in a dehydrothermal crosslinking can be advantageous from an economic point of view, but they are known in particular to be essential for gentle processing and the protection of temperature-sensitive ingredients (e.g. unstable active ingredients). A further advantage of the process according to the invention is the use of a so-called one-pot process by adding the crosslinker to the collagen suspension and then carrying out freeze-drying directly to give the crosslinked end product with a short standing time (pot time) of the collagen/crosslinker mixture of preferably not more than 24 hours before the concluding freeze-drying. A markedly more economical procedure is thereby possible overall.

Accordingly, it was possible to achieve the above object in particular by providing a process for the preparation of mechanically stable and degradation-stabilised, biocompatible epoxy-crosslinked collagen matrices containing uncrosslinked soluble collagen and peptide constituents which can be released on use, the process comprising the following steps:
 a) preparation of an aqueous collagen suspension,
 b) adjustment of the pH value of the collagen suspension from step a) to pH <4, c) optional addition of further structure-forming agents, active ingredients and/or auxiliary substances,
d) addition of an epoxy-functional crosslinking agent, the order of steps c) and d) being variable,
e) freezing of the collagen mixture obtainable from step d),
f) freeze-drying of the frozen mixture from step e) at a freeze-drying temperature <100° C.,
g) optional adjustment of the freeze-dried crosslinked collagen material so obtainable to a moisture content of <25 wt. %, based on the freeze-dried collagen material, and
h) optional conversion of the materials obtainable from step g) into the desired form, sterilisation and/or processing.

The present invention further provides the mechanically stable and degradation-stabilised, crosslinked, biocompatible collagen matrices containing uncrosslinked, soluble collagen and peptide constituents which can be released on use, obtainable by this process.

The collagen used according to the invention to prepare the crosslinked collagen matrices is in particular of bovine, porcine, equine or human origin or is collagen produced by genetic engineering. Particularly preferably, it is collagen of bovine origin. The preparation of a particularly preferred collagen is described in DE 4048622 A1 and DE 10350654 A1 of the applicant. The process described therein for the preparation of collagen sponges comprises:

subjecting a collagen raw material to alkali treatment,
washing the resulting collagen material,
subjecting the resulting collagen to acid treatment,
washing the resulting collagen material, and
grinding the resulting collagen material, in particular using a colloid mill, wherein each of the mentioned steps can optionally be repeated several times.

There is thereby obtained an aqueous collagen suspension of so-called native acid-insoluble collagen in the form of fibres and fibrils, which additionally comprises measurable amounts of acid-soluble collagen and acid-soluble peptide constituents. The qualitative detection of such acid-soluble fractions can be carried out, for example, by means of SDS-PAGE, as described herein. This collagen suspension can then be processed by means of the process according to the invention by adjustment of the pH value to pH <4, optional addition of further structure-forming agents, cosmetic or pharmaceutical active ingredients and auxiliary substances and subsequent addition of the epoxy-functional crosslinking agent, by freeze-drying at a freeze-drying temperature <100° C., to give the product according to the invention.

The use of a solely acid-soluble collagen material, as described many times in the prior art (see, for example, U.S. Pat. No. 4,883,864), is disadvantageous over the collagen suspensions used in the process according to the invention containing predominantly acid-insoluble collagen in the form of fibres and fibrils because, in order to achieve an adequate degree of crosslinking, markedly higher amounts of crosslinking agent are necessary, by comparison, in the case of solely acid-soluble collagen. It is known that materials prepared from purely acid-soluble collagen have per se, in the wet state, inadequate mechanical strength (wet tear strength) and low degradation stability as compared with materials obtainable from acid-insoluble collagen. This is attributable substantially to the fact that acid-soluble collagen consists of individual collagen molecules, whereas acid-insoluble collagen consists substantially of collagen fibrils, which are composed of laterally arranged collagen molecules which are already naturally crosslinked with one another. These fibrils are in turn bonded laterally by natural crosslinking to form larger aggregates, the collagen fibres. Degradation of both collagen fibres that are already naturally crosslinked and of chemically crosslinked collagen fibres takes place markedly more slowly owing to the smaller relative surface area and the reduced accessibility of individual protein chains, which are included in the fibre composite.

The collagen material according to the invention is substantially collagen of type I, III and V, mainly I. The collagen suspension used in the process according to the invention, which is obtainable, for example, by the processes known from DE 3203957 A1, contains the pretreated and purified collagen material in pre-ground, homogenised and defibrated form and is present as an aqueous dispersion which represents the starting material for the preparation of the crosslinked collagen matrices according to the invention.

The dry weight of the dispersion should be approximately from 1 to 4 wt. %, preferably from 1.5 to 2.5 wt. %. The pH value of the aqueous dispersion should be <4, otherwise the pH value must be adjusted to pH <4. Adjustment of the pH value is preferably carried out with dilute hydrochloric acid. Preferably, the pH value of the aqueous collagen suspension is adjusted to pH 2.5 to 3.5, more preferably to pH 2.7 to 3.3, most particularly preferably to pH 3.

Owing to the above-described preparation, in particular owing to the grinding step, the collagen suspension so obtainable usually contains, in addition to the fibrous, native acid-insoluble collagen, preferably also acid-soluble collagen and peptide constituents which have been released by the colloid grinding and are desirable according to the invention. The amount of such acid-soluble constituents can be controlled by the process and adjusted to the desired amount. Preference is given to an amount of acid-soluble collagen and peptide constituents in the collagen suspension of up to 7 wt. %, based on the dry mass of the collagen suspension, determined by the amount by weight of the soluble constituents obtained after centrifugation at 16,000 g and then freeze-dried.

The addition of further structure-forming agents which may be present or optionally of cosmetic or pharmaceutical active ingredients and optionally of auxiliary substances as described below to the collagen composition according to the invention can be carried out at this point by addition to the aqueous collagen suspension. By adding further structure-forming agents or active ingredients from the group of the matrix proteins, extracellular matrix constituents, proteinogenic active ingredients and soluble protein or peptide constituents, etc., the amount of the above-mentioned soluble collagen and peptide constituents in the collagen suspension can naturally be increased, in particular it is thereby also possible to achieve markedly higher contents of >7 wt. % (dry mass). If a collagen suspension is used which itself contains only small amounts of acid-soluble collagens and peptides, such constituents can preferably be mixed into the suspension in the desired amount at this point.

The addition of the epoxide crosslinking agent to the collagen suspension is then carried out. It is, however, equally possible to mix in the epoxide crosslinking agent before the addition of any further structure-forming agents, active ingredients or auxiliary substances that may be present. These steps are accordingly variable in the process sequence and are in principle interchangeable.

The epoxy-functional crosslinking agent is selected from the group of the epoxide compounds (epoxides) comprising in particular diepoxides as well as polyepoxy compounds such as polyglycerol polyglycidyl ethers having a degree of polymerisation of from 1 to 3, polyol polyglycidyl ethers, glycol diglycidyl ethers, glycerol diglycidyl ethers, glycerol triglycidyl ethers, diglycerol tetraglycidyl ethers, ethylene glycol glycidyl ethers, butanediol diglycidyl ethers, such as in particular 1,4-butanediol diglycidyl ether, dicarboxylic acid diglycidyl esters, etc. The epoxy-functional crosslinking agents can be selected in particular from the group of the polyethylene glycol diglycidyl ethers according to the general formula

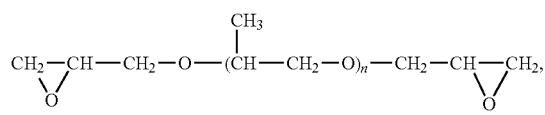

or from the group of the polyglycidyl ether-functional molecules of polyethylene glycol, polypropylene glycol and polyethylene propylene glycol, wherein the diglycidyl ether derivative is represented by the general formula

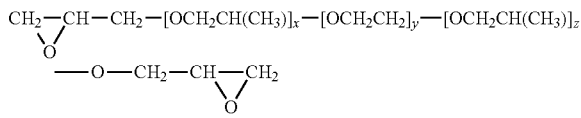

wherein x+z=0-70 and y=0-90.

The group of the diepoxides includes in particular those corresponding to the general formula

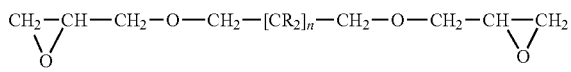

wherein R can be any substituent which does not interfere with the crosslinking process and/or reduces the water solubility of the crosslinking substance in aqueous solution and wherein n=1-6, preferably n=1-4.

In principle, the essential properties of the collagen matrices according to the invention can be controlled by the choice of the suitable epoxide crosslinking agent, for example in respect of its bifunctionality, chain length, etc.

Water-soluble epoxide crosslinking agents are preferred; the epoxide crosslinking agent is particularly preferably selected from the group of the diepoxides, 1,4-butanediol diglycidyl ether (BDDGE) being most particularly preferred. Under suitable conditions, the epoxide compounds can undergo both acid-catalysed and base-catalysed reactions with a large number of functional groups, including amine and carboxyl groups. In the prior art (e.g. Zeeman et al.), it is described that, on crosslinking in the acid pH range (pH 4-6), primarily a crosslinking of the carboxyl groups takes place, whereas in the case of alkaline crosslinking (pH 9), crosslinking takes place primarily at the amide groups.

For the incorporation of the crosslinking agent and of possible further ingredients from the group of the soluble protein and peptide constituents, as well as of active ingredients and/or auxiliary substances, the collagen suspension is preferably cooled to temperatures below room temperature (23° C.). In particular, the mixing takes place at a temperature <20° C., preferably at a temperature <10° C., particularly preferably at ≤5° C., the temperature of the collagen suspension/mixture naturally not yet being lowered to freezing of the mass at this point in the process sequence.

The above-described aqueous collagen suspension so obtained, which contains the crosslinking agent as well as optionally further structure-forming agents, active ingredients and/or auxiliary substances (collagen mixture) and has a pH value <4, is then frozen, preferably within a period of 24 hours, so that the standing time (pot time) of the aqueous collagen mixture does not exceed 24 hours if possible.

The preferred temperature of the aqueous collagen mixture during these standing times (pot times) corresponds to the above-defined reduced temperatures of the mixing operation, and the collagen mixture is accordingly maintained at a temperature <20° C., preferably <10° C., particularly preferably ≤5° C., without the collagen mixture freezing, during any standing times.

The reduced temperatures during the mixing in and the standing times of the collagen mixture before freezing surprisingly have an advantageous effect on the mechanical stability (wet tear strength) of the freeze-dried collagen matrices according to the invention. For example, it has been shown, surprisingly, that an improvement in the mechanical wet tear strength can be achieved by lowering the temperature during the standing time.

Preferably, subsequent freezing takes place over a period of from 0.5 to 4 hours, preferably from 1 to 3 hours, at a temperature of from −10 to −60° C.

Surprisingly, it has been found that longer standing times of several days, as are described in the prior art, are evidently not absolutely necessary to achieve complete and satisfactory crosslinking. By contrast, it has been shown, surprisingly, that longer standing times prior to freezing have an adverse effect in the process according to the invention on the degree of crosslinking and accordingly on the tear strength (wet tear strength) and the degradation rate. In this respect, it has been found to be advantageous to freeze the aqueous collagen mixture in the process according to the invention immediately after its preparation, within a period not exceeding 24 hours, more preferably within a period not exceeding 18 hours, particularly preferably within a period of less than 12 hours. In addition to the advantageous effects with regard to the material properties, short standing times are also preferred for reasons of process economy.

It is assumed that the crosslinking reaction between the peptide molecules and the crosslinking agent molecules in the aqueous mixture is suppressed by the immediate freezing of the aqueous suspension, which is advantageous due to the theory regarding the proceeding reaction mechanism, as explained below:

On addition of the epoxy-functional crosslinking agent to the aqueous collagen suspension, a competition reaction in principle takes place between epoxide hydrolysis (epoxide⇌$H_2O$) on the one hand and crosslinking reaction between epoxide and protein (epoxide⇌protein) on the other hand. Immediate freezing causes the reaction constituents to be immobilised and the reactions to be as it were "frozen". In addition, the water thereby freezes in highly pure form and displaces the dissolved constituents (epoxide) at the $H_2O$ crystal periphery, whereby the epoxide is localised in concentrated form relatively close to the proteins to be crosslinked. Owing to the resulting relative closeness and increased concentration of the epoxide relative to the proteins, an advantageous reaction kinetics with the collagen fibres is presumably obtained, and the competition reaction is displaced in the direction "epoxide⇌protein". It is further assumed that, with the start of the freeze-drying process, via the energy input which takes place thereby, by which the frozen water molecules are immediately converted to the gas state by sublimation, the activation energy for the reaction epoxide⇌protein, by which that reaction is set in motion, is also made available. Moreover, because the water no longer passes into the intermediate state of the liquid phase, owing to the sublimation, the competing hydrolysis reaction epoxide⇌$H_2O$ is additionally suppressed.

Accordingly, it is particularly preferred according to the invention to keep the reaction times in the aqueous suspension as short as possible and to convert the suspension into a frozen form as quickly as possible.

On the basis of the above statements, it is in particular also possible to use extremely small amounts of the epoxy crosslinker in the process according to the invention. According to the invention there are preferably used epoxy concentrations up to a maximum of 50 wt. %, preferably up to 20 wt. %, more preferably up to 10 wt. %, particularly preferably up to 7 wt. %, in each case based on the dry mass of the collagen suspension, or up to a maximum of 1 wt. %, preferably up to 0.4 wt. %, more preferably up to 0.2 wt. %, particularly preferably up to 0.14 wt. %, in each case based on the aqueous collagen suspension (which optionally also comprises further structure-forming agents, active ingredients and auxiliary substances).

In order to achieve a satisfactory degree of crosslinking (wet tear strength/degradation rate/hydrolytic stability), the crosslinking agent is preferably used in an amount of at least 0.5 wt. %, more preferably at least 1 wt. %, yet more preferably at least 3 wt. %, in each case based on the dry mass of the aqueous collagen suspension, or of at least 0.01 wt. %, preferably at least 0.02 wt. %, more preferably at least 0.06 wt. %, in each case based on the aqueous collagen suspension (which optionally also comprises further structure-forming agents, active ingredients and auxiliary substances). The choice of the suitable crosslinking agent concentration is dependent to a significant degree on the desired material properties and the particular field of application.

By contrast, the epoxide concentrations used in the prior art are many times higher. The use of such low epoxide concentrations has a particularly advantageous effect in particular on the biocompatibility, which corresponds to the residual activity of the epoxide crosslinking agent (and accordingly low toxicity) in the end product, and additionally permits the desired preservation of releasable acid-soluble collagen and peptide constituents on use of the end product.

On account of the associated toxic potential, the residual epoxide activity represents a measure of the biocompatibility of the crosslinked matrices. Determination of the residual epoxy activity can be carried out by means of a modified NBP assay (nitrobenzyl-pyridine assay) based on "Detection of Epoxides with 4-(p-nitrobenzylpyridine)" by Agarwal et al. (1979) Bull. Environm. Contam. Toxicol. 23, p. 825-829, modified according to Zocher et al. (2000) "Epoxide hydrolase activity of *Streptomyces* strains" J. Biotechnol. February 17; 77(2-3), p. 287-292, as described in detail herein.

The low residual epoxy activity, and accordingly high biocompatibility, of the collagen matrices according to the invention is presumably also attributable to the low pH value of <4 which is preferred for the process, because low pH values in the end product effect rapid hydrolysis of the remaining residual epoxide and accordingly accelerate its degradability in the end product. This effect is also significantly influenced by the moisture content of the crosslinked collagen matrices (in the end product), as explained further hereinbelow.

It has further been found, surprisingly, that the low epoxide concentrations which are preferred according to the invention have a significant influence on the tear strength, the hydrolytic stability and on the enzymatic degradation (e.g. collagenase degradation). Optimum results were achieved here in the preferred ranges defined above.

The suspension obtainable by the steps described above is preferably frozen in the form of sheets, but any configurations adapted from other conceivable geometric, natural forms or physiological forms are also possible. The thickness of the resulting sheets can be from 0.5 to 5.0 cm, preferably from 1.0 to 3.0 cm, particularly preferably from 1.5 to 2.0 cm.

The collagen matrices obtainable by the processes according to the invention are porous collagen materials, which in particular is also the reason for their high adsorption or moisture-absorbing capacity and hydration rate. The porosity of the collagen matrices according to the invention also represents a significant property for their suitability as scaffolds for cell population/cell cultivation in tissue engineering.

The degree of porosity of the collagen materials according to the invention is substantially a function of two parameters, the material density and the ice crystal size. High solids contents in the aqueous suspension increase the material density in the freeze-dried end product and reduce the rehydration agent/solid interface. High freezing gradients lead to small ice crystals, which lead to large inner material surfaces, which in turn aids rehydration. Low freezing gradients, on the other hand, cause large ice crystals, which in turn results in a large-pore material structure in the end product. The pore size of the collagen matrices according to the invention can accordingly be purposively influenced by controlling the freezing speed. Moreover, it is possible additionally to influence the pore size by adding surface-active substances, although this is less preferred.

The sheets obtained can optionally be intermediately stored at from −3° C. to −35° C. Preferably, the frozen sheets are stored for at least 24 hours.

After freezing and optional intermediate storage, the sheets are subjected to freeze-drying.

Surprisingly, it has been shown that, in the process according to the invention, the freeze-drying temperature should not exceed 100° C. in order to obtain crosslinked collagen matrices having the desired optimum properties in respect of mechanical tear strength, hydrolytic stability, biocompatibility corresponding to low residual epoxy activity, and the preservation of releasable soluble collagen and peptide constituents or releasable structure-forming agents or active ingredients from the group of the matrix proteins, extracellular matrix constituents, proteinogenic active ingredients and soluble protein or peptide constituents, etc. in the end product, and the touch-related aspects in the form of flexibility, elasticity and softness of the material.

It is known from the prior art to apply relatively high freeze-drying temperatures of from 50 to 180° C. and preferred temperatures >80° C. in order to achieve dehydrothermal crosslinking of collagen matrices. It is further known that the degree of crosslinking, and accordingly the tear strength, increases with the freeze-drying temperature. Particularly high degrees of crosslinking are achieved according to the prior art, for example, with freeze-drying temperatures between 80 and 150° C. or with temperatures above 110 to 150° C. One would accordingly assume that higher freeze-drying temperatures would also lead to better results in respect of the degree of crosslinking and accordingly the tear strength in connection with the use of crosslinking agents. On the contrary, it has been found, however, that in the epoxide crosslinking process according to the invention, higher freeze-drying temperatures lead to poorer results in respect of the tear strength (wet tear strength). In particular, it was also found that a dehydrothermal post-crosslinking at temperatures >100° C. has an adverse effect on the wet tear strength.

This effect was surprising in that the person skilled in the art would expect an additive effect of chemical crosslinking and dehydrothermal crosslinking.

It is assumed that the advantage of the freeze-drying temperatures of <100° C. according to the invention is determined by the associated lengthening of the sublimation process. Owing to the comparatively lower freeze-drying temperatures, an extended sublimation process to complete drying of the material is necessary, as a result of which an extended time period for the complete reaction of the crosslinking agent and the peptide molecules is available. Accordingly, completion of the crosslinking reaction is possible during that prolonged sublimation process, which leads to higher degrees of crosslinking, whereas high freeze-drying temperatures lead to an accelerated crosslinking reaction which then takes place inhomogeneously and unevenly, resulting in end products with low tear strength. Accordingly, the process according to the invention is carried out with a freeze-drying temperature <100° C., a freeze-drying temperature <85° C. being more preferred and <80° C. being yet more preferred.

As already stated above, freeze-drying temperatures >100° C., as are advantageous in order to achieve satisfactory dehydrothermal crosslinking, are disadvantageous in terms of the preservation of releasable soluble collagen and peptide constituents and/or structure-forming agents or active ingredients from the group of the matrix proteins, extracellular matrix constituents, proteinogenic active ingredients and soluble protein or peptide constituents, on the one hand because those components are crosslinked at the same time and accordingly inseparably bonded in the material, and on the other hand because an undesirable—at least partial—thermal denaturing of those proteinogenic constituents can take place at temperatures which are too high.

According to the crosslinking processes described in the prior art, wherein freeze-drying temperatures in the range from 20 to 30° C. are used, comparatively long crosslinking times, up to 44 hours, that is to say several days (up to 7 days), are necessary before the freeze-drying. In the process according to the invention, on the other hand, no additional crosslinking times are required prior to the freeze-drying, the standing time of the collagen suspension before the freeze-drying is carried out is not more than 24 hours, and the crosslinking then takes place substantially in the course of the freeze-drying process. In particular, it has been found that a freeze-drying temperature ≥40° C., preferably ≥50° C., more preferably ≥60° C., is advantageous for an optimum process. Because the crosslinking reaction in the process according to the invention takes place substantially during the freeze-drying, higher crosslinking temperatures, as defined above, permit particularly short freeze-drying times and accordingly particularly short crosslinking times without adversely affecting the degree of crosslinking and accordingly the resulting material stability. Moreover, the time advantage is also obtained from carrying out the crosslinking reaction and the freeze-drying in a single step.

In the process according to the invention, the moisture content of the resulting freeze-dried crosslinked collagen material is then optionally adjusted to a moisture content of up to a maximum of 25 wt. %, based on the freeze-dried collagen material (re-hydration). More preferably, an adjustment is made to a moisture content of up to 20 wt. %, yet more preferably up to 15 wt. %, in each case based on the freeze-dried collagen material. Preferably, re-hydrationor adjustment of the moisture content is carried out to at least 3 wt. %, more preferably to at least 5 wt. %, yet more preferably to at least 7 wt. %, in each case based on the freeze-dried collagen material. In particular, it is advantageous to adjust the moisture content to a content of from 3 to 25 wt. %, more preferably from 5 to 20 wt. %, yet more preferably from 7 to 15 wt. %, in each case based on the freeze-dried collagen material. The re-hydration or adjustment of the moisture content can in principle be carried out by known processes for climatisation or moisture adjustment. For example, the freeze-dried collagen materials according to the invention can be correspondingly adjusted or conditioned by storage under suitable, climate-controlled ambient conditions, for example at a temperature of from 10 to 25° C., a relative humidity of from 40 to 95%, more preferably from 50 to 75%, for a suitable period of time, for example from 5 to 120 hours, more preferably from 12 to 80 hours. In principle, a person skilled in the art is capable of suitably combining the mentioned parameters temperature, humidity and storage time in order to achieve the best possible results in respect of the desired moisture adjustment.

Surprisingly, it has been found that such an adjustment of the moisture content of the freeze-dried collagen materials is advantageous in respect of the residual activity of the epoxide crosslinking agent in the freeze-dried material. In particular, it has been possible to show, by means of the determination method defined herein, that the reduction of the residual epoxy activity to a no longer detectable level could be markedly accelerated by suitably choosing the re-hydration conditions (moisture content, storage time). In particular, it is accordingly possible, by choosing the re-hydration parameters, purposively to control the depletion of the residual epoxy activity and accordingly influence the process in an economically advantageous manner.

The resulting epoxy-crosslinked freeze-dried collagen matrices according to the invention are preferably porous, sponge-like shaped articles which can optionally be cut into a suitable shape, sterilised and processed.

The conversion of the collagen materials into the desired form according to step h) is advantageously carried out by cutting. In principle, they can be cut into any desired geometric shape or thickness using conventional, known processes.

Sterilisation of the collagen matrices according to the invention is important for therapeutic applications in particular, reference being made to conventional processes here too. Sterilisation by means of gamma/X-radiation is preferred.

Processing includes optionally printing, embossing, stamping, perforation and/or lamination as well as optionally laser engraving (changing the surface structure) of the collagen matrices according to the invention, as well as packaging.

The porous collagen matrices according to the invention are preferably provided in the form of a layered material which has a thickness (dimension which has the smallest longitudinal extent) of preferably approximately from 0.1 to 30 mm, preferably from 0.5 to 20 mm, yet more preferably from 1 to 10 mm.

The crosslinked collagen matrices according to the invention can contain, in addition to collagen, optionally at least one further constituent which is selected from the group consisting of further structure-forming agents, cosmetic or pharmaceutical active ingredients and/or auxiliary substances.

From the group of further structure-forming agents, alginates, elastin, hyaluronic acid are preferably chosen.

Cosmetic active ingredients within the scope of the invention include in particular those active ingredients which are intended to be applied externally to humans for the purpose of cleansing, care or for influencing the appearance or body odour or for imparting odour impressions, unless they are intended primarily for alleviating or eliminating diseases, afflictions, physical injuries or pathological complaints. Within this context, the materials according to the invention for cosmetic use are, for example, bath preparations, skin washing and cleansing agents, skin care agents, in particular facial skin care agents, cosmetics for the eyes, lip care agents, nail care agents, foot care agents, hair care agents, in particular hair shampoos, hair conditioners, hair softeners, etc., screening agents, skin tanning and lightening agents, depigmenting agents, deodorants, antihydrotics, depilatory agents, insect repellents, etc. or such agents in combination. Use as a cosmetic dressing or mask is particularly preferred.

Examples of compounds having cosmetic, optionally also, for example, dermatological, therapeutic activity include: anti-acne agents, antimicrobial agents, antiperspirants, astringents, deodorants, depilatory agents, conditioning agents for the skin, skin-smoothing agents, agents for increasing skin hydration such as, for example, dexpanthenol (panthenol, pantothenol), glycerol or urea as well as other NMFs (natural moisturising factors) such as, for example, pyrrolidonecarboxylic acid, lactic acid and amino acids, sunscreens, keratolytics, radical acceptors for free radicals, antioxidants, antiseborrheics, anti-dandruff agents, antiseptic active ingredients, active ingredients for treating the signs of skin ageing and/or agents which modulate skin differentiation and/or proliferation and/or pigmentation, protease inhibitors, for example MMP (matrix metalloproteinase) inhibitors, glycation inhibitors for reducing the formation of AGE (advanced glycation end-product) substances, vitamins such as vitamin C (ascorbic acid) and its derivatives, such as, for example, glycosides such as ascorbyl glucoside, or esters of ascorbic acid such as sodium or magnesium ascorbyl phosphate or ascorbyl palmitate and stearate, L-ascorbic acid phosphate esters, alkali metal salts, such as sodium and potassium salts, of L-ascorbic acid phosphate esters; alkaline earth metal salts, such as magnesium and calcium salts, of L-ascorbic acid phosphate esters; trivalent metal salts, such as aluminium salts, of L-ascorbic acid phosphate esters; alkali metal salts of L-ascorbic acid sulfate esters, such as sodium and potassium salts of L-ascorbic acid sulfate esters; alkaline earth metal salts, such as magnesium and calcium salts, of L-ascorbic acid sulfate esters; trivalent metal salts, such as aluminium salts, of L-ascorbic acid sulfate esters; alkali metal salts, such as sodium and potassium salts, of L-ascorbic acid esters; alkaline earth metal salts, such as magnesium and calcium salts, of L-ascorbic acid esters; and trivalent metal salts, such as aluminium salts, of L-ascorbic acid esters, any natural, nature-identical and artificial peptides such as, for example, neuropeptides, antimicrobial peptides and matrikines with and without modification by covalent bonding to a fatty acid or esterification.

Active ingredients having an irritant side-effect, such as alpha-hydroxy acids, β-hydroxy acids, alpha-keto acids, β-keto acids, retinoids (retinol, retinal, retinic acid), anthralins (dioxyanthranol), anthranoids, peroxides (in particular benzoyl peroxide), minoxidil, lithium salts, antimetabolites, vitamin D and its derivatives; catechols, flavonoids, ceramides, polyunsaturated fatty acids, essential fatty acids (e.g. gamma-linoleic acid), active ingredients having liposomal structures, carrier systems, enzymes, coenzymes, enzyme inhibitors, hydrating agents, skin-calming agents, detergents or foam-forming agents, and inorganic or synthetic mattifying fillers, or decorative substances such as pigments or colourings and colouring particles for foundations, make-up formulations, and other agents for the cosmetic embellishment and colouring of the eyes, lips, face, etc., as well as abrasive agents.

Mention may further be made of plant active ingredient extracts or extracts or single substances obtained therefrom. The plant active ingredient extract is generally selected from the group consisting of solid plant extracts, liquid plant extracts, hydrophilic plant extracts, lipophilic plant extracts, single plant ingredients; as well as mixtures thereof, such as flavonoids and their aglyca: rutin, quercetin, diosmin, hyperoside, (neo)hesperidine, hesperitin, *gingko biloba* (e.g. gingko flavone glycosides), *crataegus* extract (e.g. oligomeric procyanidines), buckwheat (e.g. rutin), *Sophora japonica* (e.g. rutin), birch leaves (e.g. quercetin glycosides, hyperoside and rutin), elderflowers (e.g. rutin), lime-tree blossom (e.g. ethereal oil with quercetin and farnesol), St. John's Wort oil or St. John's Wort extract, evening primrose oil (e.g. olive oil extract), *calendula*, arnica (e.g. oily extracts of the blossom with ethereal oil, polar extracts with flavonoids), melissa (e.g. flavones, ethereal oil); immune stimulants: *Echinacea purpurea* (e.g. alcoholic extracts, fresh plant juice, pressed juice), *Eleutherococcus senticosus*; alkaloids: caffeine, theine, black tea or black tea extract, theobromine, capsaicin, ajmaline (e.g. prajmaline), evergreen (e.g. vincamine); further phytopharmaceuticals: aloe, horse chestnut (e.g. aescine), garlic (e.g. garlic oil), pineapple (e.g. bromelain), ginseng (e.g. ginsenosides), milk thistle fruit (e.g. standardised Silymarin extract), butcher's broom root (e.g. ruscogenin), valerian (e.g. valepotriates, tct. valerianae), kava-kava (e.g. kavalactones), hop flowers (e.g. hop bitter substances), extr. passiflora, enzian (e.g. ethanol. extract), anthraquinone-containing drug extracts, e.g. aloin-containing aloe vera juice, pollen extract, algae extracts, liquorice root extracts, palm extract, galphimia (e.g. mother tincture), mistletoe (e.g. aqueous-ethanol. extract), phytosterols (e.g. beta-sitosterol), mullein flowers (e.g. aqueous-alcohol. extract), drosera (e.g. liqueur wine extract), sea-buckthorn fruit (e.g. juice obtained therefrom or sea-buckthorn oil), marshmallow root, primrose root extract, fresh plant extracts from hollyhock, comfrey, ivy, horse tail, yarrow, ribwort (e.g. pressed juice), stinging nettle, celandine, parsley; plant extracts from *Norolaena lobata, Tagetes lucida, Teeoma siems, Momordica charantia*, and aloe vera extracts, Cardiospermum mother tincture, dulcamara extract, as well as tanning agents and tannin.

Unlike the active ingredients described above, which are used substantially in cosmetics, the therapeutic active ingredients (medicaments) are those which, within the meaning of pharmaceutical law, are intended inter alia for healing, alleviating or preventing diseases, ailments, physical injuries or pathological complaints. Suitable according to the invention are in particular those agents and active ingredients which are intended for external or transdermal application, in particular in the field of wound treatment and healing and in the field of the treatment of burns, in particular for first aid for burns.

Active ingredients for dermal or transdermal application are in particular skin-active but also transdermal active ingredients. They include, for example: agents for the treatment of burns, agents for the treatment of skin diseases, analgesics for external application, for example dextropropoxyphen, pentazocine, pethidine, buprenorphine; antirheumatics/antiphlogistics (anti-inflammatories) (NSARs), for example frankincense or frankincense extract, indometacin, diclofenac, naproxen, ketoprofen, ibuprofen, flurbiprofen, salicylic acid and derivatives thereof, such as acetylsalicylic acid, oxicams; steroid hormones, for example corticoids and glucocorticoids such as hydrocortisone, cortisol, cortisone acetate, cloprednol, prednisone, prednisolone, deflazacort, fluocortolone, triamcinolone, betamethasone, betamethasone valerate, mometasone furoate, dexamethasone, methylprednisolone, ethynyloestradiol, medroergotamine, dihydroergotoxine;

antigout agents, for example benzbromarone, allopurinol; external dermatic agents, antihistamines such as brompheniramine, bamipine; antibiotics such as erythromycin, clindamycin, tetracycline, including antibacterial agents such as, for example, colloidal silver and silver salts such as silver chloride, silver nitrate, silver iodide or further silver-containing wound treatment agents known from the prior art; antimycotics, peptide medicaments, antiviral active ingredients, anti-inflammatory active ingredients, antipruritic active ingredients such as anaesthetising active ingredients, for example antihistamines, benzocain, polidocanol or corticoids and glucocorticoids; anti-acne agents; antiparasitic active ingredients; hormones for external application; vein therapeutics; immune suppressants such as calcineurin inhibitors such as tacrolimus and pimecrolimus, mineral substances and trace elements, such as, for example, inorganic or organic selenium compounds, zinc and zinc salts, etc., all for dermal or transdermal application.

By way of clarification it is noted that the classification of the active ingredients into the group of the cosmetic or therapeutic active ingredients within the context of the present invention does not represent a conclusive classification. In particular, the classification made here does not exclude the possibility that the corresponding active ingredients are used as both cosmetic and also therapeutic active ingredients.

Preferred active ingredients for dermal and transdermal application are selected from the group containing: agents for the treatment of skin diseases such as neurodermatitis, atopic dermatitis, psoriasis, rosacea, etc., anti-inflammatory active ingredients, antipruritic active ingredients, tanning agents, topical analgesics, anaesthetics and antibacterial active ingredients.

Particularly preferably, at least one active ingredient is selected from the group of the skin-like lipids, comprising, for example, phospholipids, neutral lipids and sphingolipids as well as components of the natural moisturising factor (NMF) of the skin, comprising, for example, urea, amino acids and carboxylic acids, pyrrolidonecarboxylic acid, sodium, potassium, calcium, magnesium, lactate (lactic acid), citrate, chloride, phosphate, etc., uric acid and other organic acids.

Particular preference is further given to those active ingredients which are used in the field of wound treatment, in particular for the treatment of chronic wounds, decubitus, Ulcus cruris, diabetic foot syndrome, etc., such as, for example, analgesics, for example immune suppressants, hormones, anaesthetising active ingredients, antiparasitic, fungicidal or antimycotic and antibacterial active ingredients such as in particular silver-containing active ingredients such as, for example, silver nitrate, silver chloride, silver iodide, micro-sized silver particles or further silver-containing wound treatment substances known from the prior art, active ingredients for supporting and regulating the wound environment such as in particular electrolytes, silica, mineral substances and trace elements such as, for example, potassium, magnesium, calcium, selenium, iodine, etc., active ingredients for achieving a wound debridement such as, for example, collagenases or other suitable proteolytic enzymes known in the prior art, as well as active ingredients for assisting wound healing such as, for example, growth factors, enzyme inhibitors, matrix proteins or extracellular matrix constituents or soluble (low molecular weight) protein and peptide constituents, collagen types other than the type I, III and V collagens already contained in the collagen suspension used according to the invention.

Particularly preferred active ingredients from the field of the wound treatment agents are selected from silver-containing active ingredients such as in particular silver nitrate, silver chloride, micro-sized silver particles, tacrolimus, pimecrolimus, antihistamines, polidocanol, frankincense/frankincense extract, capsaicin, tannin, St. John's Wort oil/St. John's Wort extract, evening primrose oil, dexpanthenol as well as inorganic or organic selenium compounds, zinc and zinc salts.

Further preferred active ingredients are those from the group of the proteinogenic active ingredients, preferably comprising growth factors, proteinogenic hormones, enzymes, coenzymes, glycoproteins, blood clotting factors, other cytokines and variants of the above-mentioned active ingredients prepared by recombinant techniques.

Growth factors which can be used according to the invention are preferably selected from the group consisting of VEGF (vascular endothelial growth factor), bFGF (basic fibroblast growth factor), FGF-1 (acid fibroblast growth factor), TGF-β, TGF-α (transforming growth factor β or α), EGF (endothelial growth factor), HGF (hepatocyte growth factor), TNF-α (tumor necrosis factor α), IGF I and II (insulin-like growth factor/insulin binding growth factor I and II), heparin binding growth factor I and II, PDGF (platelet derived growth factor), PD-ECGF (platelet derived endothelial cell growth factor), BMP (bone morphogenetic growth factor), GHRP (growth hormone release factor), cartilage inducing factor A and B, bone growth factors, interleukin 8, angiopoietin, angiogenin, aprotinin, and vWF (von Willebrand factor).

Glycoproteins as active ingredients include, for example, immunoglobulins and antibodies.

Other cytokines as active ingredients include, for example, interleukins and interferon.

Further preferred active ingredients are those which have a haemostatic action, such as blood clotting factors such as, for example, thrombin, fibrinogen or cholesteryl sulfate (e.g. sodium cholesteryl sulfate), or active ingredients having an activating action on factors and substances of the extrinsic and/or intrinsic clotting cascade, such as, for example, phospholipids, kaolin, aprotinin, concentrates of factor or factors, tissue factor or calcium ions.

It is further conceivable to administer further active ingredients such as bronchial therapeutics such as antiasthmatics, antitussives, mucolytics, etc., antidiabetics such as, for example, glibenclamide, hormones, steroid hormones such as dexamethasone, cardiac glycosides such as digitoxin, cardiac and circulatory therapeutics such as, for example, beta blockers, antiarrhythmics, antihypertensives, calcium antagonists, etc., psychopharmaceuticals and antidepressants such as, for example, tricylcic antidepressants (NSMRI), serotonin reuptake inhibitors (SSRI), noradrenaline reuptake inhibitors (NRI), serotonin-noradrenaline reuptake inhibitors (SNRI), monoaminooxidase inhibitors (MAO inhibitors), etc., neuroleptics, anticonvulsives or antiepileptics, hypnotics, sedatives, anaesthetics, gastric, intestinal therapeutics, lipid-lowering agents, analgesics such as, for example, antimigraine agents, paracetamol, salicylic acid and derivatives thereof such as acetylsalicylic acid, diclophenac, ibuprofen, ketoprofen, naproxen, etc., antiphlogistics, vasodilators, diuretics, antigout agents, cytostatics, muscle relaxants, contraceptives, for example in the form of hormone patches, anti-addiction agents in the form of, for example, nicotine patches, plant extracts, provitamins such as, for example, beta-carotene, vitamins such as, for example, vitamin C, A, B, E, etc., by transdermal administration in a composition according to the invention, for example in the form of a transdermal active ingredient patch.

It is most particularly preferred according to the invention to add as further structure-forming agents or active ingredients substances which are selected from the group of the matrix proteins, extracellular matrix constituents or soluble (low molecular weight) protein and peptide constituents, preferably from the group comprising elastin, elastin hydrolysates, glycosaminoglycans, such as heparan sulfate, chondroitin sulfate, dermatan sulfate, keratan sulfate, heparin and hyaluronic acid, proteoglycans, such as aggrecan, fibromodulin, decorin, biglycan, versican, perlecan, high-density basal membrane proteoglycan, syndecan and serglycine, fibrin, fibronectin, glucans, such as paramylon, etc. Most particularly preferred extracellular matrix constituents and structure-forming agents of that type are elastin and elastin hydrolysates, hyaluronic acid and fibronectin.

The collagen material per se can also have certain therapeutic actions, such as in particular a haemostatic action or a positive assisting effect in wound healing. It is, however, not an active ingredient within the meaning of the invention.

The above-mentioned active ingredients are present in the crosslinked collagen matrices on their own or in a combination of a plurality of active ingredients, preferably in an amount of advantageously up to 40 wt. %, preferably up to 60 wt. %, more preferably up to 80 wt. %, based on the freeze-dried end product.

In the freeze-dried collagen matrices, structure-forming agents or active ingredients from the group of the matrix proteins, extracellular matrix constituents, proteinogenic active ingredients and soluble protein or peptide constituents, together with any acid-soluble collagen and peptide constituents from the working up of the collagen suspension used, can preferably account in total for up to 10 wt. %, more preferably up to 20 wt. %, based on the dry mass of the freeze-dried end product, measured by the determination method (BCA) defined herein.

The collagen matrices according to the invention can optionally contain at least one auxiliary substance.

Auxiliary substances include: agents for adjusting the pH, such as buffers, inorganic and organic acids or bases; fatty substances, such as mineral oils, such as paraffin oils or Vaseline oils, silicone oils, vegetable oils such as coconut oil, sweet almond oil, apricot oil, corn oil, jojoba oil, olive oil, avocado oil, sesame oil, palm oil, eucalyptus oil, rosemary oil, lavender oil, pine oil, thyme oil, mint oil, cardamom oil, orange blossom oil, soya oil, bran oil, rice oil, rape oil and castor oil, wheatgerm oil and vitamin E isolated therefrom, evening primrose oil, plant lecithins (e.g. soya lecithin), sphingolipids/ceramides isolated from plants, animal oils or fats, such as tallow, lanolin, butter oil, neutral oil, squalane, fatty acid esters, esters of fatty alcohols such as triglycerides, and waxes having a melting point corresponding to the temperature of the skin (animal waxes, such as beeswax, carnauba wax and candelilla wax, mineral waxes, such as microcrystalline waxes, and synthetic waxes, such as polyethylene or silicone waxes), as well as all oils suitable for cosmetic purposes (so-called cosmetic oils), as mentioned, for example, in the CTFA paper, Cosmetic Ingredient Handbook, 1st Edition, 1988, The Cosmetic, Toiletry and Fragrance Association, Inc., Washington, surface-active agents in addition to the wash surfactants mentioned above, such as dispersing agents, humectants, emulsifiers, etc.; fillers; stabilisers; cosolvents; pharmaceutically and cosmetically conventional or other colourings and pigments, in particular those which are used primarily for colouring the hydrogel composition and not for application to and colouring of the human body, such as those pigments and colourings like the decorative colourings listed under the group of the active ingredients; preservatives; emollients; lubricants and glidants, etc.

Preferred auxiliary substances according to the invention are fats and oils. Preference is given in particular to cosmetic oils as listed above, in particular triglycerides, particularly preferably caprylic/caproic acid triglycerides, squalane or jojoba oil as well as evening primrose oil.

The auxiliary substances mentioned above are present in the crosslinked collagen matrices on their own or in a combination of a plurality of auxiliary substances, preferably in an amount of advantageously up to 80 wt. %, preferably up to 60 wt. %, more preferably up to 40 wt. %, based on the freeze-dried end product.

In general, the classification of the substances mentioned above into the category of the auxiliary substances within the context of the present invention does not rule out the possibility that these auxiliary substances can also have certain cosmetic and/or therapeutic actions, which is true in particular for the mentioned cosmetic oils which are preferably used.

If the collagen materials according to the invention contain a combination of additional ingredients from at least two of the mentioned groups, structure-forming agents, active ingredients and/or auxiliary substances, then the total amount of these additional ingredients in the porous collagen carrier matrix overall is up to 40 wt. %, preferably up to 60 wt. %, more preferably up to 80 wt. %, in each case based on the freeze-dried collagen material.

The amount of such structure-forming agents, active ingredients and/or auxiliary substances, either alone or in a combination of at least two of the mentioned groups, is preferably not less than 0.1 wt. %, more preferably not less than 1 wt. %.

As already stated, a further advantage of the process according to the invention is that, because of the special procedure, in particular also the low residual epoxide activity due to the process and the possibility of inactivating any residual activities by adjusting the moisture content after freeze-drying, it is not necessary to wash out the epoxide crosslinker, as is known, for example, from processes of the prior art (e.g. Zeeman group). This is important not only in order to preserve the acid-soluble collagen and peptide constituents of the collagen suspension used releasably in the freeze-dried, crosslinked material, but also for further structure-forming agents or active ingredients from the group of the matrix proteins, extracellular matrix constituents, proteinogenic active ingredients and soluble protein or peptide constituents, as defined herein, for example elastin, etc., which are additionally added to the collagen suspension. In order for such constituents to be able to develop their positive action on use, they must be releasable from the crosslinked collagen matrix, which acts almost as a carrier material, on use. It is imperative therefor that such proteinogenic active ingredients and constituents remain predominantly uncrosslinked in the material and are not crosslinked in the collagen material, for example by the addition of epoxy, and thereby inseparably bonded. By means of the process according to the invention it is possible to introduce these soluble matrix protein constituents in uncrosslinked form into the collagen material and to preserve them predominantly uncrosslinked therein, inter alia also because an extremely small amount of epoxide crosslinking agent is present in the process according to the invention. As a result of this small amount of crosslinking agent, the crosslinking reaction takes place primarily between the small amounts of the epoxide crosslinking agent and the collagen polypeptides present in excess as reaction partners, instead of with the low molecular weight proteinogenic matrix molecules.

Overall, the amount of such soluble, uncrosslinked, proteinogenic constituents which can be released on use in the collagen matrices according to the invention is at least 0.1 wt. %, preferably at least 2 wt. %, particularly preferably ≥5 wt. %, in each case based on the dry mass of the freeze-dried collagen material. The amount of such releasable soluble constituents, comprising acid-soluble collagen and peptide constituents and/or structure-forming agents or active ingredients from the group of the matrix proteins, extracellular matrix constituents, proteinogenic active ingredients and soluble protein or peptide constituents, is advantageously a maximum of up to 20 wt. %.

The quantitative amount of such soluble releasable collagen and peptide constituents can be determined, for example, by means of BCA assay (bichinoic acid assay) in comparison with bovine serum albumin as standard in the supernatant after extraction in 0.9% NaCl over a period of 24 hours at 37° C., as described in detail herein.

In processes according to the prior art, such soluble proteinogenic constituents would also be crosslinked because of the large amount of crosslinking agent and would accordingly be inseparably bonded to the carrier material. Any uncrosslinked residues would additionally be washed out of the material in the further process by the necessary washing out of the residual epoxide crosslinker in order to reduce the residual epoxy activity.

In a particularly preferred embodiment of the process, no synthetic hydrophilic polymer, in particular no functionally activated synthetic hydrophilic polymer, such as, for example, a glycol, such as in particular a difunctionally activated polyethylene glycol, is added to the collagen suspension prior to the addition of the crosslinking agent. Accordingly, particularly preferred embodiments of the crosslinked collagen matrices according to the invention are those which do not comprise a conjugate of a collagen with a synthetic polymer.

As stated above, the freeze-dried epoxy-crosslinked collagen matrices according to the invention no longer exhibit detectable residual epoxy reactivity, measured by the method described herein, at the latest after the step of moisture adjustment.

In addition, it has also been shown that the collagen materials obtainable by the process according to the invention do not exhibit any toxicity in in vitro standard processes for toxicity determination (XTT test), which is further evidence of the high biocompatibility of such crosslinked collagen materials.

The freeze-dried epoxy-crosslinked collagen matrices according to the invention are additionally distinguished by improved degradation stability, corresponding to a reduced degradation rate (reduced collagenase degradation/collagenase digestion), improved hydrolytic stability and increased mechanical stability in the sense of improved wet tear strength, in each case as defined and described hereinbelow.

Because the degradation speed, or degradation rate, reflects the stability of collagen matrices to enzymatic degradation, in particular to collagenase digestion, it can be determined, for example, by means of a collagenase digestion test. In this test, degradation of the collagen fibres and fibrils by the enzyme collagenase (collagenase from *Clostridium histolyticum* (type 1) in PBS (phosphate-buffered saline) buffer) is purposively brought about under controlled conditions and, after a defined reaction time, the amount of decomposition products is determined by means of UV/VIS measurement in a spectral photometer, as described in detail in the following examples.

The degradation-stabilised collagen matrices according to the invention are distinguished by a reduction in the degradation rate, in the sense of a reduction in the amount of soluble decomposition products, as compared with uncrosslinked or only dehydrothermally crosslinked freeze-dried collagen, which can be determined by means of the collagenase digestion test as described herein.

The degradation rate is on the one hand dependent on the amount of crosslinking agent used, but on the other hand is also dependent on the amount of any soluble protein constituents (matrix proteins, etc.) added. Owing to the process parameters used, the degradation properties can be controlled in dependence on the desired field of application.

The collagen matrices according to the invention preferably have a degradation rate, measured at the reaction time of 6 hours after addition of the collagenase, of not more than 85%, preferably not more than 70%, more preferably not more than 50%, as compared with uncrosslinked or only dehydrothermally crosslinked freeze-dried collagen (degradation rate 100%). This means an improvement in the degradation stability of at least 15%, preferably at least 30%, particularly preferably at least 50%, as compared with uncrosslinked or only dehydrothermally crosslinked collagen.

In a further method for determining the degradation rate of the collagen matrix, the degradation speed of the collagen matrix is determined by determining the weight of a sample before and after enzymatic degradation by collagenase from *Clostridium histolyticum* (type I, Worthington Biochemicals). To that end, defined pieces of the collagen matrices are immersed in a solution which contains defined units of collagenase in 1 ml of PBS (pH 7.2) and are incubated for 2 hours at 37° C. with gentle shaking. The degradation is stopped by addition of 0.2 ml of a 0.25 M EDTA solution, and cooling on ice is carried out for 10 minutes. The sample is then washed with 5 ml of PBS buffer (pH 7.2) three times for 15 minutes and with 5 ml of demineralised water three times for 15 minutes, frozen overnight at −80° C. and then freeze-dried. After the freeze-drying, the weight of the partially degraded collagen carrier sample is determined and the degradation speed is determined as follows:

Degradation speed (%)=100×(original weight−weight after degradation)/original weight The collagen matrices according to the invention are distinguished by a degradation speed of not more than about 60%, more preferably not more than about 50%, yet more preferably not more than about 40%, and the degradation speed is preferably at least about 2%, more preferably at least about 4%, yet more preferably at least about 8%, yet more preferably at least about 10%.

Depending on the degree of crosslinking, the crosslinked collagen matrices according to the invention are materials which are resorbable more or less quickly. That is to say, a material having a low degree of crosslinking is degraded enzymatically under the conditions prevailing in the organism after subcutaneous or intramuscular administration, for example. After being brought into contact with the wound, the material can accordingly remain thereon or therein and aid healing of the wound. Removal of the material is advantageously not necessary. Such an application is advantageous in particular when used as a wound treatment agent. If such wound treatment agents are intended to remain in the wound, they are also referred to as degradable implants.

As well as having increased mechanical stability (tear strength), a crosslinked collagen material has increased stability to biodegradability (for example enzymatic degradation) and is suitable in particular as a semi-permanent implant for tissue reconstruction or for defect filling or as a scaffold for cell population, for example in the field of tissue engineering.

A low degradation speed, and accordingly high degradation stability, of the collagen matrices is advantageous in particular also for use as a cosmetic dressing, cell population scaffold or for use as a sponge material for absorbing wound exudate, for example in a vacuum-assisted wound treatment therapy.

On the other hand, however, too low a degradation rate of the matrix for use as a wound treatment agent and as a degradable wound treatment implant is undesirable because it can lead to encapsulation of the incompletely degraded material in the wound or in the body and accordingly to the occurrence of undesirable hardening of the tissue. It is therefore particularly important according to the invention to adjust the degradation speed/rate optimally for the desired application. The degradation properties of the collagen material are influenced both by the nature of the material obtained as described above and by the crosslinking or drying conditions applied thereto during the preparation of the collagen matrices according to the invention. According to the invention, particularly advantageous degradation properties can be achieved with the collagen material prepared as described above, in particular in combination with the preferred preparation conditions for the collagen matrix that are described hereinbelow, in dependence on the desired field of application.

In particular collagen materials for use as a cosmetic dressing, as a scaffold for cell population in tissue engineering and as a dressing material for use in a vacuum-assisted wound treatment therapy have a lower degradation rate of not more than 50%, which corresponds to an improvement in the degradation stability of at least 50%, as compared with uncrosslinked or only dehydrothermally crosslinked collagen. On the other hand, collagen materials for use as a wound treatment agent or as a degradable wound treatment agent that is to remain in the wound (degradable implant) or as an implant for tissue reconstruction as well as for lining deep skin defects have a lower degradation rate of not more than 85 to 70%, which corresponds to an improvement in the degradation stability of at least 15 to 30%, as compared with uncrosslinked or only dehydrothermally crosslinked collagen.

Within the scope of the present invention, crosslinking effect or degree of crosslinking means on the one hand the reduction in the degradation rate, or an increase in the degradation stability of the collagen matrix, which can be achieved by the crosslinking and, on the other hand, the improvement in mechanical stability by the increase in the tear strength (wet tear strength), which can in principle be determined by conventional determination methods, in particular by the methods described herein, and, in addition, the increase in the rigidity of the material, which is quantifiable by measuring the modulus of elasticity.

For example, the resistance of a collagen structure to collagenase can be determined, for example, by the method described herein (collagenase digestion), which is a measure of the crosslinking, uncrosslinked material being enzymatically degraded considerably more quickly than is the case with crosslinked material.

The hydrolytic stability is also a measure of the crosslinking of a collagen matrix and can be demonstrated, for example, by placing a defined amount of collagen material in an aqueous solution and determining the change in the material properties over time. While uncrosslinked or dehydrothermally crosslinked collagen materials exhibited complete hydrolysis (structural dissolution of the matrix structure) after <18 days under the chosen conditions (aqueous solution at 50° C.), no structural changes to the matrix were observed in the case of the crosslinked collagen materials according to the invention under the same conditions.

The wet tear strength of the collagen matrices according to the invention can be determined according to DIN EN ISO 3376 and is preferably >50 cN/mm layer thickness, more preferably >100 cN/mm, yet more preferably >300 cN/mm.

Preferably, however, the wet tear strength is determined using an internal measuring method (UV8801) as described in the following examples. Preferred wet tear strengths of the crosslinked collagen matrices according to the invention, determined by this internal method (UV 8801), are >200 cN/mm layer thickness, more preferably >400 cN/mm, yet more preferably >500 cN/mm.

The freeze-dried epoxy-crosslinked collagen matrices according to the invention additionally exhibit a markedly improved absorption, liquid absorption and storage capacity as well as an increased moisturisation or hydration rate as compared with uncrosslinked collagen matrices, and as compared with collagen matrices which have been crosslinked only by means of dehydrothermal crosslinking or by means of other known chemical crosslinking agents.

The liquid absorption or storage capacity of the collagen matrices according to the invention denotes the ability to absorb amounts of liquid in particular in combination with the ability to store and retain such absorbed amounts of liquid. According to the invention, preference is given to those crosslinked collagen matrices which are capable of absorbing and storing amounts of liquid of from 1 to 200 times, preferably from 10 to 100 times, their own weight.

A measure of the amount of liquid which can be absorbed by the material is denoted by the mass degree of swelling ($Q_m$):

$$Q_m = \frac{m_{Gel}}{M_{tr.pr.}}$$

where $Q_m$ denotes the ratio of the mass of the swollen material ($m_{Gel}$) to the mass of the dry material prior to swelling ($m_{tr.Pr.}$).

In order to measure the mass degree of swelling, the freeze-dried material is accordingly weighed and then placed into a dish containing an excess of distilled water at a temperature of from 15 to 25° C., on the surface of the water, and allowed to swell for 10 minutes. The excess water is poured away without mechanical action. After measuring the weight of the swollen composition again, the mass degree of swelling is calculated according to the above formula.

The freeze-dried compositions according to the invention preferably have a mass degree of swelling of from 15 to 100.

It is additionally possible to indicate the liquid retention capacity based on the weight of the composition. To that end, the increase in weight of the swollen material samples calculated in the above-described test arrangement is converted, after the excess liquid has been poured off, to the volume of liquid corresponding to that weight increase and that absorbed volume of liquid is indicated, based on 1 g of the composition used.

The collagen matrices according to the invention are also distinguished by a higher optical density as compared with uncrosslinked or only dehydrothermally crosslinked collagen matrices.

Optical density here denotes the quantitative unit optical density, measured as the common logarithm of the quotient of transmitted light intensity to irradiated light intensity, calculated using a Heiland SW densitometer TD 03 on layered collagen matrices having a layer thickness of 1 m. The collagen matrices of the present invention preferably have an optical density of ≥0.02, more preferably ≥0.03, yet more preferably ≥0.05, per mm layer thickness.

In addition to the above-mentioned advantages of the collagen matrices according to the invention, which are the result substantially of the process according to the invention, the epoxide-crosslinked collagen material according to the invention has in particular the following advantageous properties over uncrosslinked or only dehydrothermally crosslinked collagen material and over collagen materials crosslinked by means of other known chemical crosslinking agents:

- Better feel: The material is more velvety, softer, feels fuller or more voluminous than, for example, uncrosslinked/-dehydrothermally crosslinked material with an identical layer thickness. This is advantageous in the cosmetic field in particular.
- Higher optical density: advantageous in the field of cosmetic application and for embodiments which are to be evaluated by colour impressions.
- Higher return force: the crosslinked material does not collapse in the wet state in response to mechanical actions as easily as, for example, uncrosslinked/dehydrothermally crosslinked material and assumes its original volume again more easily, similarly to a sponge.
- Improved water absorption capacity
- Improved hydration rate
- High elasticity and flexibility
- Controllable cell population/cell reaction (response of the cell to the material)

In connection with the controllable cell population/cell reaction it is to be noted that, by means of the process according to the invention, a possiblity has been found of purposively controlling the material properties in respect of rigidity and flexibility, enzymatic degradability (degradation rate) and the provision of releasable soluble collagen and peptide constituents or of further matrix proteins and soluble peptide constituents, etc., as listed above.

In respect of the control of the rigidity and flexibility it is to be noted that it is known that the rigidity/flexibility of matrices suitable for cellular population has a significant influence on the properties of the cells adhering thereto. The influence of the cell environment on the development of the cell phenotype and its expression pattern, migration and proliferation behaviour has in recent years increasingly been pushed to the forefront of basic research in the field of tissue engineering. Apart from its composition, the rigidity (stiffness or rigidity) and elasticity of the extracellular matrix (ECM) is a main aspect of the particular cell environment.

The rigidity of the extracellular matrix is a regulation signal for the behaviour of cells. For example, the differentiation of stem cells is directly dependent on the rigidity of the substrate; likewise, the behaviour of myofibroblasts, for example, is based on a particular rigidity of the cell environment. The cells react directly to the mechanical feedback of the ECM surrounding them (mechano-chemical sensing).

In order to study the connection between the rigidity of the material surrounding the cells and the cell response based thereon, the use of gels of different rigidity and composition is known as prior art (Mih et al. in PLoS ONE 6 (5): e19929; 2011). Examples of synthetic substrates are polyacrylamide hydrogels of different degrees of polymerisation as well as polyelectrolyte multilayers (PEM); protein-based gels are likewise used, such as, for example, collagen gels (e.g. according to Yang et al. in Biophysical Journal Vol. 97, 2051-2060; 2009). The rigidity of the collagen gel of soluble collagen is directly dependent on the concentration of the gel-forming protein and can be further modified by additional crosslinking, for example with glutaraldehyde or also genipin.

The elasticity of the material in question is quantified by means of the so-called modulus of elasticity (also: Young's modulus), E. This is defined as follows:

The modulus of elasticity (also: Young's modulus, from the physicist Thomas Young) is a material constant from material engineering which describes the relationship between stress and strain on deformation of a solid body with linear elastic behaviour. The modulus of elasticity is abbreviated with the symbol E.

The value of the modulus of elasticity is higher, the greater the resistance of a material to deformation. A material having a high modulus of elasticity is therefore rigid, a material with a low modulus of elasticity is flexible.

It is known that the ECM rigidity in healthy and diseased or damaged tissue has a broad distribution.

For example, the rigidity of nerve tissue (brain) is E=about 2.5 kPa, that of muscle tissue is E=12 kPa and that of bones is E=18 GPa. For granulation tissue, as is present in wound healing, an initial rigidity of from 0.1 to 1 kPa and of 18 kPa after 7 days is described (Krishnan et al. in Cell Adhesion & Migration 2:2, 83-94; 2008).

It is of interest to provide scaffolds for 3D cultivation in the biotechnology, basic research and tissue engineering field which, as well as having high biocompatibility and corresponding degradation stability, also have a rigidity which is specific to the tissue in question and can purposively be adjusted in order to be able to provide the optimum cell environment for the cells that are to be cultivated.

The collagen matrices according to the invention have a rigidity, adjustable by means of the process according to the invention, in the range from 0.01 to 100 kPa, preferably in the range from 0.1 to 60 kPa, particularly preferably in the range from 2 to 40 kPa.

It is accordingly possible, by means of the present process for the crosslinking of collagen matrices, purposively to adapt the material properties to the requirements of optimum cellular ingrowth (population), cell differentiation, in particular for the so-called expression profile of the cells that are in direct contact with the matrix. Expression profile denotes, for example, the expression of particular matrix proteins, cytoskeleton proteins (actins), cytokines, proteases, etc. Such a control of cell differentiation or of the expression profile of populated matrices is advantageous in particular in the field of tissue engineering and bioimplants, but also in the establishment of model systems in basic research, diagnostics and analysis.

On account of the above-described advantageous properties of the crosslinked collagen matrices according to the invention, they are particularly suitable for cosmetic and medical, pharmaceutical or biotechnological use.

Accordingly, the invention also provides the cosmetic use of the collagen matrices according to the invention as a cosmetic agent, in particular as a cosmetic dressing or mask.

The use of a freeze-dried epoxy-crosslinked collagen matrix according to the invention as a cosmetic dressing or mask is preferably carried out either by applying the dressing or mask in the dry state to the body part to be treated and then hydrating it with water or an aqueous solution of one or more active ingredients and/or optionally auxiliary substances, or by soaking the collagen matrix in the form of a cosmetic dressing or mask with an aqueous solution of one or more active ingredients and/or optionally auxiliary substances before it is applied to the body part to be treated.

A corresponding dry or pre-moistened application can also be carried out when using the collagen matrices according to the invention as an agent for wound treatment.

The present invention relates further to the freeze-dried epoxy-crosslinked collagen matrices according to the invention for use as a pharmaceutical agent (including also medical devices), in particular for topical or dermal application or for implantation in humans or animals.

Particular preference is given to the use of the collagen matrices according to the invention as an implant, as a dermal or transdermal skin treatment agent and/or as a haemostatic agent and as a scaffold for cell cultivation in the tissue engineering field.

The present invention relates further to the collagen matrices according to the invention for use in at least one indication or application selected from the following group, which consists of: treatment of acute or chronic wounds, improvement of wound healing, equalising tissue defects, lining deep skin defects while building volume, assisting tissue regeneration, regeneration of the dermis, treatment of burns, use in plastic surgery, use after scar excision, combination therapy with autologous split-skin transplants, assisting the formation of granulation tissue, assisting angiogenesis, ensuring better scar quality, treatment of chronic wounds such as Ulcus cruris, decubitus and diabetic foot, treatment of open wounds, treatment of wound healing disorders, treatment of diseases with deep skin defects, production of a jaw implant, production of a bone implant, production of a cartilage implant, production of a tissue implant, production of a skin implant, production of a medical dressing, production of a transdermal dressing, production of a wound plaster, production of a wound bandaging material, production of a wound dressing and production of a cell culture matrix for cell multiplication for the implantation of cell matrix units, and in biotechnology in the production of model systems for the in vitro reproduction of tissue systems (e.g. skin model) for basic research, diagnostics and analysis.

Furthermore, the collagen matrices according to the invention can also be used in vacuum-assisted wound treatment therapy, as is known in principle from the prior art and as described, for example, in US 2007/0027414. Because of their high flexibility, the collagen matrices according to the invention can successfully be introduced into the wound bed in such a vacuum treatment, where they positively assist the removal of excess wound fluids owing to their good absorption and hydration properties. Transport of the exudate is already achieved on the one hand by the permeable, porous collagen matrix material owing to its fundamentally high hydrophilicity and swellability. In addition, the collagen matrices according to the invention have high porosity, as a result of the freeze-drying process, which additionally facilitates the passage of liquids. It is an additional advantage that the collagen matrices according to the invention per se already have a positive influence on the wound healing process, in particular also because of the releasable soluble collagen, peptide and protein constituents contained therein.

The collagen matrices according to the invention are particularly suitable for the above applications in particular also because of their high biocompatibility, corresponding to the low residual epoxy activity, and the releasable soluble collagen, peptide and protein constituents they contain.

For the above-described preferred fields of application of the crosslinked collagen matrices according to the invention, they are preferably in the form of layered masks, sheets, matrices, dressings, pads, layers or similar flat forms. Such layered forms are particularly suitable for the external and flat treatment also of larger affected regions of the skin.

In a further possible embodiment, such layered collagen matrices can also be completely or partially laminated, that is to say present in the form of mutually bonded multilayer layers (sandwich layer). There can be used as laminates conventional materials known from the prior art, such as, for example, fibres, nonwovens, nets, films or foils of suitable materials such as, for example, rayon, cellulose, polyethylene (PE) or polyurethane (PU) or other synthetic or semi-synthetic polymers/copolymers, which can be firmly bonded to the carrier materials within the scope of the present invention by conventional methods, for example by adhesive bonding, hot lamination, crosslinking, etc. Such a lamination is particularly suitable for additionally increasing the mechanical stability of the layered collagen materials according to the invention, as well as for improving the handling thereof during application, in particular in the moistened state. A preferred lamination comprises a lamination with a self-adhesive layer or a layered plaster material, which is preferably applied to the layered collagen materials in such a manner that the self-adhesive laminate layer projects wholly or partly beyond the collagen material at the edges, so that the laminated collagen materials, similarly to a conventional plaster arrangement, can readily be fixed to the area of skin to be treated by means of the self-adhesive lamination projecting at the edges. In the case of such self-adhesive laminated collagen materials, particular preference is given to those self-adhesive laminated coatings which are particularly well tolerated by the skin, have a low tendency to cause irritation and allergies and are easy to remove, in order not to cause additional damage on removal of the adhesive layer to areas of skin which may already be damaged or irritated. Depending on the desired field of use, such laminations can be occlusive, semi-occlusive or hydrophilic and non-occlusive, preference being given to hydrophilic, non-occlusive or at most (in the sense of "at most still") semi-occlusive laminations, in order to permit hydration of the laminated collagen materials for use. Furthermore, when choosing such self-adhesive lamination coatings it must be ensured that the adhesive layer is not water-soluble, so that the adhesive cannot be dissolved when moistening the material and the adhesive or fixing action is thus not lost.

Accordingly, the present invention also comprises in particular layered crosslinked collagen materials which are provided wholly or partially with a further layer selected from fibres, nonwovens, nets, films or foils or a self-adhesive layer, which is applied to the layered collagen material in such a manner that it finishes therewith at the edges or projects wholly or partly beyond the collagen material at the edges.

As stated above, the collagen matrices according to the invention can be pre-soaked, that is to say fully rehydrated, both before cosmetic use and before medical use. Such soaking or rehydration is preferably carried out with an aqueous solution selected from the group comprising water and optionally demineralised water or so-called thermal water, physiological solutions and aqueous solutions which contain at least one active ingredient and/or auxiliary substance. The aqueous solutions used for soaking or rehydration are also referred to as activator solutions.

Such activator solutions can be, for example, solutions of readily volatile active ingredients and/or auxiliary substances which, on account of the preparation process, for example the freeze-drying, should not or cannot be introduced into a freeze-dried material, such as, for example, certain fractions of ethereal oils, perfumes, etc. There can also be present active ingredients and/or auxiliary substances which achieve an additional hydrating action and which, on account of this hydrating action or on account of hygroscopic tendencies, cannot be incorporated into the freeze-dried collagen matrices according to the invention, or can be incorporated in only small amounts, because the stability of the freeze-dried collagen material itself, or the stability of any moisture-unstable active ingredients that are present, can no longer be maintained.

In principle, one or more of the active ingredients and/or auxiliary substances mentioned hereinbefore can be present in the activator solutions. In particular, active ingredient solutions that contain one or more of the preferred active ingredients or auxiliary substances mentioned hereinbefore are particularly suitable for therapeutic use in the indications that are preferred according to the invention.

In a particularly preferred embodiment, an aqueous activator solution which is substantially free of preservatives and/or auxiliary substances from the group of the polyethers, polyethylene glycols (PEGs), polypropylene glycols (PPGs) and polyglycols (PGs) is used.

In a further preferred embodiment of the invention, the epoxy-crosslinked collagen material according to the invention is present with the activator solution in an associated, spatial arrangement (combination preparation, application kit, set, kit-of-parts, etc.). Such combination preparations or kit-of-part arrangements preferably comprise at least one of the collagen matrices according to the invention, preferably those in the form of layered dressings, pads or masks, as well as at least one aqueous solution which can contain one or more active ingredients and/or at least one or more auxiliary substances (activator solution).

The configuration of such combination preparations or kit-of-parts combinations of collagen material according to the invention on the one hand and activator solution on the other hand can provide for the two components to be removed from the kit-of-parts arrangement separately and combined for further use outside it. It is, however, also conceivable for the components to be combined within the kit-of-parts packaging itself, for example in chambers provided therefor, and the rehydrated composition then to be brought directly therefrom to further external or transdermal use. This can preferably be carried out directly by the end user.

The invention is explained in greater detail by the following examples.

EXAMPLES

Example 1

Preparation Example 1a

Pure Collagen Matrix with Epoxide Crosslinking
(5% Epoxide Crosslinking Agent/Dry Mass)

Example for the preparation of an epoxy-crosslinked collagen biomatrix according to the invention without addition of further soluble protein or peptide constituents, active ingredients and/or auxiliary substances, using an amount of epoxide crosslinking agent of 5%, based on the dry mass of the collagen suspension.
 a) Provision of 3000 g of a collagen suspension (dry content collagen: 1.6%, collagen content: 48 g), prepared by the process according to DE 4048622 A1 and in particular DE 10350654 A1.
 b) Adjustment of the pH value of the collagen suspension to pH 3.3.
 c) (omitted)
 d) At a temperature below 10° C., 2.4 g of 1,4-butanediol diglycidyl ether (BDDGE, Sigma-Aldrich) are added dropwise to the collagen suspension within a period of 5 minutes, while stirring with a paddle stirrer (eurostar, IKA) at 600 rps. The resulting mass is degassed in a vacuum mixer (Smartmix, Amann/Girrbach) in portions of about 750 g.
 e) Within 2 hours of mixing in the crosslinking agent, the degassed suspension is poured out in sheets and frozen, the collagen suspension being maintained at a temperature <18° C. until frozen.
 f) The frozen mass is then stored for 24 hours at −20° C. and then subjected to freeze-drying, the freeze-drying temperature being maintained below 100° C.
 g) The lyophilised collagen matrix is re-hydrated to a moisture content of up to 25%, based on the dried collagen matrix, at a humidity of 60-70% rel. humidity over a period of 24-48 hours.
 h) The collagen matrix so obtained is split into layers of 1-2 mm, processed and optionally subjected to gamma sterilisation (20 kGy).

Preparation Example 1b

Pure Collagen Matrix with Epoxide Crosslinking
(10% Epoxide Crosslinking Agent/Dry Mass)

Example for the preparation of an epoxy-crosslinked collagen biomatrix according to the invention without addition of further soluble protein or peptide constituents, active ingredients and/or auxiliary substances, using an amount of epoxide crosslinking agent of 10%, based on the dry mass of the collagen suspension.

The preparation is carried out analogously to Preparation example 1a, wherein in step d) 4.8 g of 1,4-butanediol diglycidyl ether (BDDGE, Sigma-Aldrich) are added and in step g) the re-hydration is carried out for up to 96 hours.

Example 2

Preparation Example 2a

Epoxide-Crosslinked Collagen Matrix with
Additional Soluble Protein Constituents from the
Group of the Matrix Proteins (Elastin Hydrolysate)
(5% Epoxide Crosslinking Agent/Dry Mass)

Example for the preparation of an epoxy-crosslinked collagen biomatrix according to the invention with addition of further soluble protein/peptide constituents (matrix proteins: elastin) using an amount of epoxide crosslinking agent of 5%, based on the dry mass of the aqueous collagen suspension.
 a) Provision of 3000 g of a collagen suspension (dry content collagen: 1.6%, collagen content: 48 g), prepared by the process according to DE 4048622 A1 and in particular DE 10350654 A1.
 b) Adjustment of the pH value of the collagen suspension to pH 3.3.
 c) At a temperature below 10° C., 2.4 g of 1,4-butanediol diglycidyl ether (BDDGE, Sigma-Aldrich) are added dropwise to the collagen suspension within a period of 5 minutes, while stirring with a paddle stirrer (eurostar, IKA) at 550 rps.
 d) Then addition of 30 g of elastin hydrolysate (Elastin spezial B1N, GfN, Herstellung von Naturextrakten GmbH) under the same conditions. The resulting mass (aqueous collagen mixture) is degassed for 2×5 minutes in a vacuum mixer (Smartmix, Amann/Girrbach) in portions of about 750 g.
 e) Within 2 hours of mixing in the crosslinking agent and the elastin hydrolysate, the degassed collagen mixture is poured out in sheets and frozen, the collagen mixture being maintained at a temperature <10° C. until frozen.

f) The frozen mass is then stored for 24 hours at −20° C. and then subjected to freeze-drying, the freeze-drying temperature being maintained below 100° C.

g) The lyophilised collagen matrix is re-hydrated to a moisture content of up to 25%, based on the dried collagen matrix, at a humidity of 60-70% rel. humidity over a period of 24-48 hours.

h) The collagen matrix so obtained is split into layers of 1-2 mm, processed and optionally subjected to gamma sterilisation (20 kGy).

Preparation Example 2b

Epoxide-Crosslinked Collagen Matrix with Additional Soluble Protein Constituents from the Group of the Matrix Proteins (Elastin Hydrolysate) (10% Epoxide Crosslinking Agent/Dry Mass)

Example for the preparation of an epoxy-crosslinked collagen biomatrix according to the invention with addition of further soluble protein/peptide constituents (matrix proteins; elastin), using an amount of epoxide crosslinking agent of 10%, based on the dry mass of the aqueous collagen suspension.

The preparation is carried out analogously to Preparation example 2a, wherein in step c) 4.8 g of 1,4-butanediol diglycidyl ether (BDDGE, Sigma-Aldrich) are added and in step g) the re-hydration is carried out for up to 96 hours.

Example 3

Preparation Example 3

Epoxide-Crosslinked Collagen Matrix with Additional Active Ingredients/Auxiliary Substances from the Group of the Cosmetic Fats and Oils (Triglycerides/Neutral Oil) (4.8% Epoxide Crosslinking Agent/Dry Mass)

Example for the preparation of an epoxy-crosslinked collagen biomatrix according to the invention with addition of further active ingredients/auxiliary substances from the group of the fats and oils (triglycerides/neutral oil), using an amount of epoxide crosslinking agent of 4.8%, based on the dry mass of the aqueous collagen suspension.

a) Provision of 3900 g of a collagen suspension (dry content collagen: 1.6%, collagen content: 62.4 g), prepared by the process according to DE4048622 A1 and in particular DE 10350654 A1.

b) Adjustment of the pH value of the collagen suspension to pH 3.3.

c) At a temperature below 10° C., 2.95 g of 1,4-butanediol diglycidyl ether (BDDGE, Sigma-Aldrich) are added dropwise to the collagen suspension within a period of 5 minutes, while stirring with a paddle stirrer (eurostar, IKA) at 550 rps.

d) Then addition of 3.8 g of neutral oil under the same conditions. The resulting mass (aqueous collagen mixture) is degassed for 2×5 min in a vacuum mixer (Smartmix, Amann/Girrbach) in portions of about 750 g.

e) Within 2 hours of mixing in the crosslinking agent and the neutral oil, the degassed collagen mixture is poured out in sheets and frozen, the collagen mixture being maintained at a temperature <10° C. until frozen.

f) The frozen mass is then stored for 24 hours at −20° C. and then subjected to freeze-drying, the freeze-drying temperature being maintained below 100° C.

g) The lyophilised collagen matrix is re-hydrated to a moisture content of up to 25%, based on the dried collagen matrix, at a humidity of 60-70% rel. humidity over a period of 24-48 hours.

h) The collagen matrix so obtained is split into layers of 1-2 mm, processed and optionally subjected to gamma sterilisation (20 kGy).

Example 4

Qualitative Determination of Soluble Proteins by Means of SDS-PAGE

Brief explanation: SDS-PAGE

SDS=sodium dodecyl sulfate, detergent, sodium salt of a long-chained fatty acid

PAGE=polyacrylamide gel electrophoresis, electrophoresis in a polymer gel of acrylamide Electrophoresis: Separation of charged particles in a carrier substance by application of an electric voltage, which results in migration of the particles.

Brief description: By addition of ionic detergents at pH >7 uncharged proteins are converted to charged particles, which separate in a gel by application of an electric voltage in the resulting electric field on the basis of their size and shape along a migration distance. Proteins of low mass migrate more quickly than large proteins of higher mass. Spherical proteins migrate more quickly than elongate, thread-like proteins. The protein groups separate according to size and form narrow stripes (called bands) in the gel, which can be visualised with specific dyes. The size of proteins or protein fragments is assessed visually on the basis of their migration distance as compared with reference substances (molecular weight standard=proteins of known size).

Suitable test systems are conventional commercially available standard test systems such as, for example, the Criterion system from Biorad:

Criterion XT Precast Gel 4-12% acrylamide,
Buffer system: Bis-Tris, 12+2 Well Comb, 45 µl per well
Gel thickness: 1 mm, catalogue 345-0123 Bio Rad
Buffer B: Criterion XT Mes (buffer, 20×) Control 210007145
Sample buffer: XT Sample Buffer; 4×, 10 ml Control 310008088

Staining of the finished protein gels is achieved by the ready-to-use reagent GelCode Blue Safe Stain (Thermo Scientific), which is based on the protein-sensitive dye Coomassie Blue.

Example 5

Quantitative Determination of Soluble Protein Constituents by Means of the BCA Method The detection of soluble proteins and protein constituents by means of the BCA test is based on the fact that proteins form a complex with $Cu^{2+}$ ions in alkaline solution (biuret reaction). The $Cu^{2+}$ ions of this complex are reduced to $Cu^+$ ions, which form a violet colour complex with bicinchonic acid (BCA). The absorption of this colour complex is measured by spectrometry at 562 nm. The reduction is carried out by the side chains of cystein, tyrosine, tryptophan and the peptide bond, the intensity of the colour formation (the redox behaviour of the groups involved) being dependent inter alia on the temperature, so that the sensitivity of the test can be modified by variation thereof.

Suitable test systems are conventional commercially available standard test systems such as, for example, the Pierce BCA Protein Assay Kit (Thermo Scientific).

The determination is made in comparison with a standard solution of BSA (bovine serum albumin).

Reaction conditions for colour development: 60° C., 1 hour reaction time.

Test Results:

FIG. 1 shows the percentage of soluble protein constituents in an epoxy-crosslinked collagen matrix with additional soluble matrix proteins (elastin hydrolysate), corresponding to the composition according to Preparation examples 2a and 2b, which were crosslinked with epoxide concentrations of 5% and 10%, in each case based on the dry mass of the collagen suspension, in comparison with a solely dehydrothermally crosslinked collagen matrix with elastin hydrolysate (100%). (In the figure, "uncrosslinked" denotes a dehydrothermally crosslinked (i.e. not chemically crosslinked) collagen matrix.) The figure clearly shows that, despite chemical crosslinking, a high proportion of soluble protein constituents and matrix proteins is retained in the material. The measurement additionally showed the following amounts by weight of soluble protein constituents, in each case based on the freeze-dried end product, for the tested materials:

Dehydrothermally crosslinked collagen matrix with elastin ("uncrosslinked"): >15 wt. %

Preparation example 2a with 5% epoxide: >10 wt. %

Preparation example 2b with 10% epoxide: >4 wt. %.

Example 6

Determination of the Degradation Rate Collagenase Digestion Test

The determination of the enzymatic stability (degradation stability) of collagen matrices is carried out by means of a method which is based on the degradation of the collagen fibres by the enzyme collagenase. In this method, the degradation of the collagen fibres and fibrils by the enzyme collagenase (collagenase from *Clostridium histolyticum* (type 1) in PBS buffer (phosphate-buffered saline)) is effected purposively under controlled conditions, and the amount of decomposition products is determined by means of UV/VIS measurement in a spectrophotometer after a defined reaction time.

Chemicals Used:

TRIS buffer solution: TRIZMA base (Fluka Art No. 93350 LOT 450756/1), $CaCl_2 \cdot 6H_2O$ (Riedel de Haen Art No. 12074 LOT 12610), HCl 25% (Merck Art No. 1.00316.1000 LOT Z730816335)

EDTA solution: ethylenediamine-tetraacetic acid disodium salt dihydrate 0.2 mol/l (Fluka Art No. 03679 LOT 1104109 10505293)

collagenase: Sigma C 688T LOT 122 k8607, 700 U/mg collagen matrices: e.g. according to Preparation examples 1 to 3

Preparation of the Reagents:

TRIS buffer solution 0.1 M/25 mM $CaCl_2$:

1.21 g of TRIZMA base are dissolved together with 0.55 g of $CaCl_2 \cdot 6H_2O$ in 80 ml of RO water and adjusted to a pH value of 7.4 with about 1 ml of 25% HCl. The solution is then transferred to a 100 ml measuring flask and made up with RO water.

EDTA Solution 0.2 mol/l:

3.7224 g of ethylenediamine-tetraacetic acid disodium salt dihydrate are dissolved in 50 ml of RO water (using a magnetic stirrer about 30 minutes).

Enzyme Solution:

5 mg of the enzyme are dissolved in 1 ml of TRIS buffer solution. For the individual tests, aliquots of 50 or 100 U (charge-dependent volume, here=35 and 70 µl) are added to the test system.

Acetic Acid 0.95%:

0.95 ml of glacial acetic acid is made up to 1000 ml with RO water.

Procedure:

Pieces having a radius of 10 mm (dry weight about 15 mg) are cut out of 2 mm thick collagen sheets and dried for 12 hours in an exsiccator. The samples are weighed into 2 ml Eppendorf vessels (Safe Lock Tubes 0030.120.094), and 1.5 ml of the TRIS buffer solution are added. As soon as 35 µl of enzyme solution have been added, the samples are tempered at 37° C. in a Thermoblock (Stuart Scientific block heater).

After the corresponding digestion time (1.5 hours, 3 hours, 6 hours and 23 hours), 200 µl of EDTA solution are added to the Eppendorf vessels and centrifugation is carried out at maximum capacity for 40 minutes at 18° C. For dilution with 7.5 ml of glacial acetic acid 0.95%, aliquots of 800 µl are transferred to 10 ml standard-ground test tubes, sealed with a stopper and moved gently from side to side for homogenisation purposes.

Photometric Measurement:

Measurement is carried out in a UV/VIS spectrophotometer at a wavelength of 234 nm. 10 mm quartz cuvettes are used. 7.5 ml of acetic acid with 800 µl of TRIS buffer solution is measured as the blank value. Before the samples are measured, a corresponding enzyme solution (here: 35 µl of enzyme solution in 1.5 ml of TRIS buffer in an Eppendorf vessel, of which 800 µl in 7.5 ml of acetic acid) should be measured as the zero value, the absorption of which is set as the zero value in the diagram (absorption about 0.0166).

For the determination of the absolute values, a calibrating solution is also prepared and measured according to the above procedure.

Preparation of the Calibrating Solution:

0.1006 g of collagen was degraded completely overnight at 37° C. in 8 ml of TRIS buffer with 233 µl of collagenase solution (corresponding to 600 U). On the following day, 1333 µl of EDTA solution were added to the solution, and it was made up to 10 ml with TRIS buffer in the measuring flask. Corresponding volumes of this solution, according to the following table, were diluted to 10 ml with 0.95% acetic acid and the absoprtion of this solution was measured at 234 nm.

| 1% collagen solution [ml/10 ml] | Mass of collagen degradation product in g | Concentration of collagen [µg/ml] | A (234 nm) (MW; n = 2) |
|---|---|---|---|
| 0 | 0 | 0 | −0.0146 |
| 0.3 | 0.0003 | 300 | 0.2782 |
| 0.6 | 0.0006 | 600 | 0.6095 |
| 0.9 | 0.0009 | 900 | 0.9754 |
| 1.2 | 0.0012 | 1200 | 1.3254 |

The corresponding calibration curve has the linear equation $$A(234 \text{ nm}) = 0.0011c - 0.0407 (R^2 = 0.9983).$$

Figure 2A:
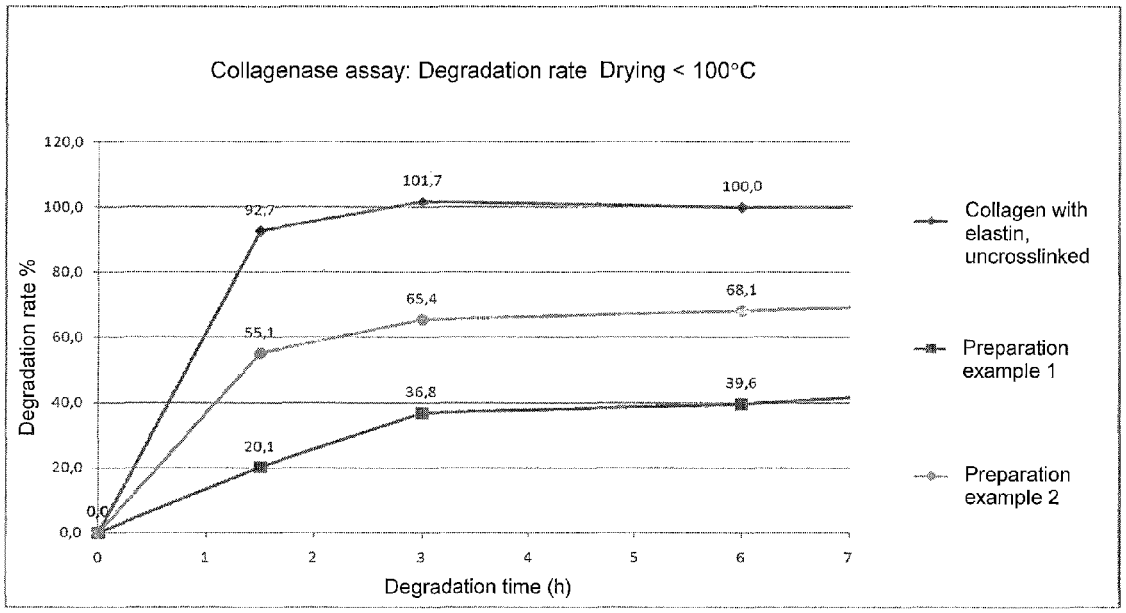

Test Results:

FIG. 2a shows the relative degradation rates (%) of an epoxy-crosslinked collagen matrix without additional ingredients according to Preparation example 1a and of an epoxy-crosslinked collagen matrix with additional soluble matrix proteins (elastin hydrolysate) according to Preparation example 2a (epoxide concentration 5% in each case) in comparison with a solely dehydrothermally crosslinked collagen matrix with elastin hydrolysate. (In the figure, "uncrosslinked" denotes a dehydrothermally crosslinked (i.e. not chemically crosslinked) collagen matrix.)

The figure clearly shows the improvement in the degradation as a reduction in the degradation rate (reduction in enzymatic degradation) of the epoxide-crosslinked collagen materials according to the invention.

The matrix dissolved completely after 6 hours was set as 100% here. The absorption values were normalised to 10 mg of matrix.

By determining the calibration curve, the absolute values of the dissolved amounts can be calculated from the absorption values:

| | Concentration of the dissolved matrix in mg/ml and degradation in % | | | | |
|---|---|---|---|---|---|
| | t = 0 | t = 1.5 h | t = 3 h | t = 6 h | t = 23 h |
| uncrosslinked | 0 | 9.37 | 10 | 10 | 10 |
| | 0% | 93.7% | 100% | 100% | 100% |
| Ex. 1a | 0 | 2.64 | 4.18 | 4.45 | 7.64 |
| | 0% | 26.4% | 47.8% | 44.5% | 76.4% |
| Ex. 2a | 0 | 5.88 | 6.84 | 7.09 | 8.73 |
| | 0% | 58.8% | 68.4% | 70.9% | 87.3% |

Figure 2B:
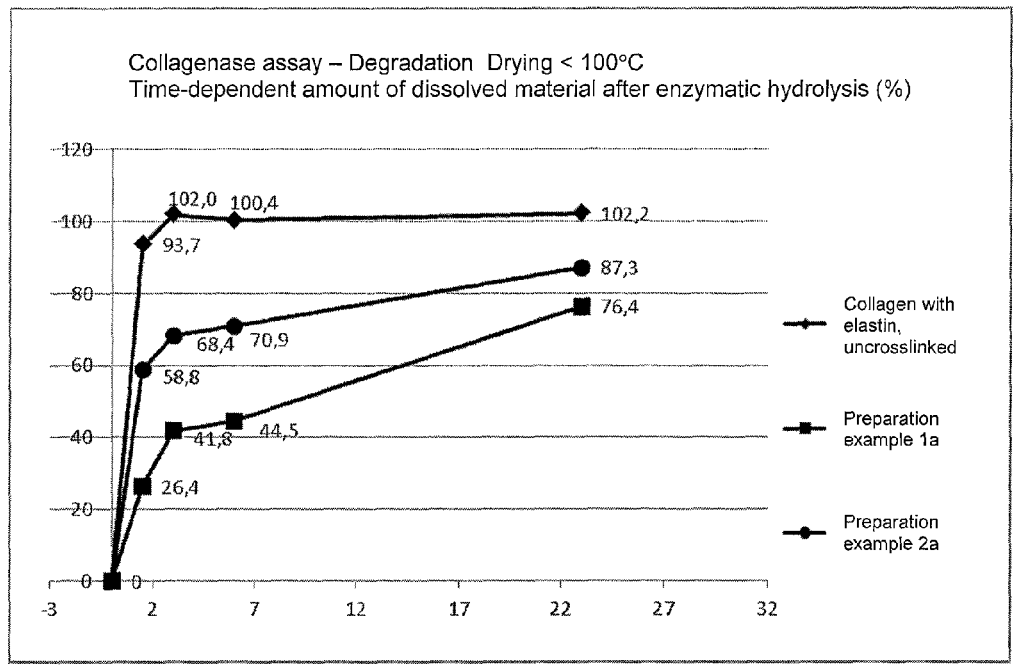

FIG. 2b shows the corresponding absolute concentrations of the dissolved matrix normalised to 10 mg of matrix used over a period of up to 23 hours.

FIG. 2b additionally shows the development of the degradation over a period of up to 23 hours as the percentage of the degradation. The collagen matrices crosslinked according to the invention accordingly exhibit markedly better degradation stability than a chemically uncrosslinked matrix even after 23 hours' collagenase digestion.

Example 7

Determination of the Hydrolytic Stability

The hydrolytic stability of collagen matrices is studied by placing a defined collagen material in an aqueous solution and storing it at 50° C. and determining the change in the material properties over time.

An example of an aqueous solution for studying the hydrolytic stability has the following composition:

| | Manufacturer | Amount (%) |
|---|---|---|
| Glycerol | Merck | 2.50 |
| 1,5-Pentanediol | Merck | 2.40 |
| Rokonsal MEP | ISP | 0.250 |
| Sodium chloride | AppliChem | 0.10 |
| Ultrapure water | | 94.75 |

Preparation:
1) Dissolve glycerol, pentanediol and Rokonsal MEP in a glass beaker using a magnetic stirrer
2) Make up to about 98% of the final amount with ultrapure water (SHC 101), with stirring
3) Add NaCl and dissolve using a magnetic stirrer
4) Adjust pH value to pH 5.0 with 1% citric acid solution
5) Make up to the final amount with ultrapure water (SHC 101)
6) Check pH value and adjust to pH 5.0 again if necessary The hydrolytic stability can be determined on the one hand by measuring the reduction in surface area, caused by shrinkage of the matrices.

The hydrolytic stability can additionally be determined by means of the decrease in mass, determined according to $$\text{Hydrolytic stability (\%)} = M_{tx} \times 100 / M_{t0}$$

where $M_{tx}$ = mass of the dried intact/cohesive matrix material
$M_{t0}$ = mass of the dry matrix material before the start of the test Test Results:

The hydrolytic stability was studied under the above-described conditions by determining the reduction in surface area of a) dehydrothermally crosslinked collagen matrix ("uncrosslinked") containing triglycerides/neutral oil, which was freeze-dried at a freeze-drying temperature >120° C., b) epoxy-crosslinked collagen matrix according to the invention of Preparation example 3 (containing triglycerides/neutral oil), and c) epoxy-crosslinked collagen matrix (5% epoxide/DM) corresponding to the composition according to Preparation example 3 (containing triglycerides/neutral oil), which was freeze-dried at a freeze-drying temperature >120° C.

Figure 3:
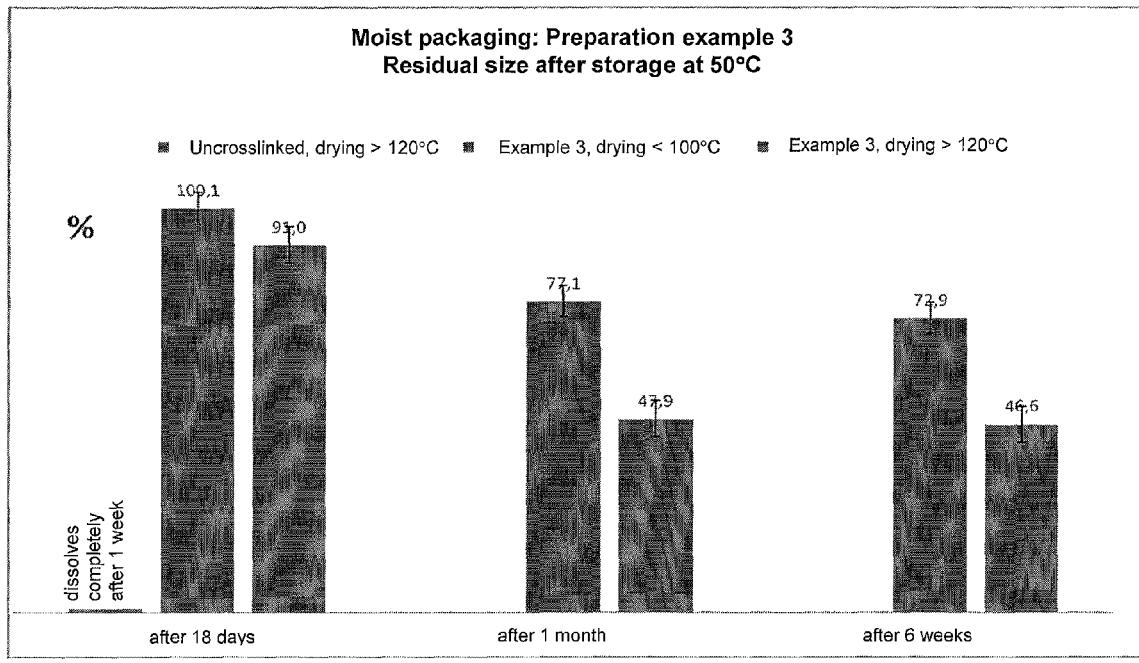

FIG. 3 shows that merely dehydrothermally crosslinked collagen materials ("uncrosslinked") according to a) exhibit complete hydrolysis (structural dissolution of the matrix structure) after only 5 days under the chosen test conditions, whereas in the case of the epoxy-crosslinked collagen materials according to the invention according to b), no structural changes in the matrix are observed even after 18 days under the same conditions. At the same point in time, epoxy-crosslinked collagen materials dried at freeze-drying temperatures >100° C. according to c) exhibit the start of hydrolysis (shrinkage of the surface area) as compared with the materials according to the invention according to b). After about 4 weeks, a matrix according to the invention according to b) also exhibits the start of hydrolysis, the materials according to c) dried at a higher temperature exhibiting a markedly poorer hydrolytic stability at that time. The results accordingly reflect the fact that the freeze-drying temperature also has an influence on hydrolytic stability. Accordingly, matrices exposed to a freeze-drying temperature >100° C. exhibit poorer hydrolytic stability as compared with the materials produced according to the invention (freeze-drying temperature <100° C.).

Figure 4:
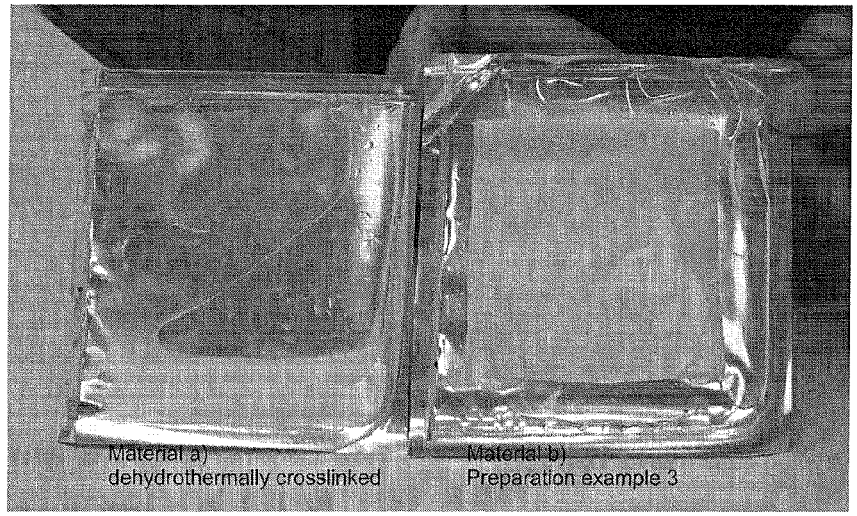

By way of example, FIG. 4 shows the degree of hydrolysis of a dehydrothermally crosslinked matrix according to a) as compared with a matrix according to the invention according to b) after 18 days' storage under the test conditions described hereinbefore.

Example 8

Determination of Wet Tear Strength Internal Method (UV8801)

In the method for determining the tear strength by means of a die (internal measuring method UV8801), a metal die having a spherical head (25 mm in diameter) is pressed onto a layered embodiment of the collagen matrices according to the invention with the aid of a mechanical tester (Zwick material tester B Z 2.5/TN 1S), and path and force which the die leaves behind and exerts are recorded.

For the determination, a layered collagen matrix having a thickness of 1.5 mm is cut to a size of 8×8 cm and introduced into the specimen receiver of the device and completely wetted therein. The measurement is then started and the spherical die is pressed onto the sample until the material tears.

The force at which the material tears is recorded by means of electronic data recording, calculated and displayed.

Figure 5:
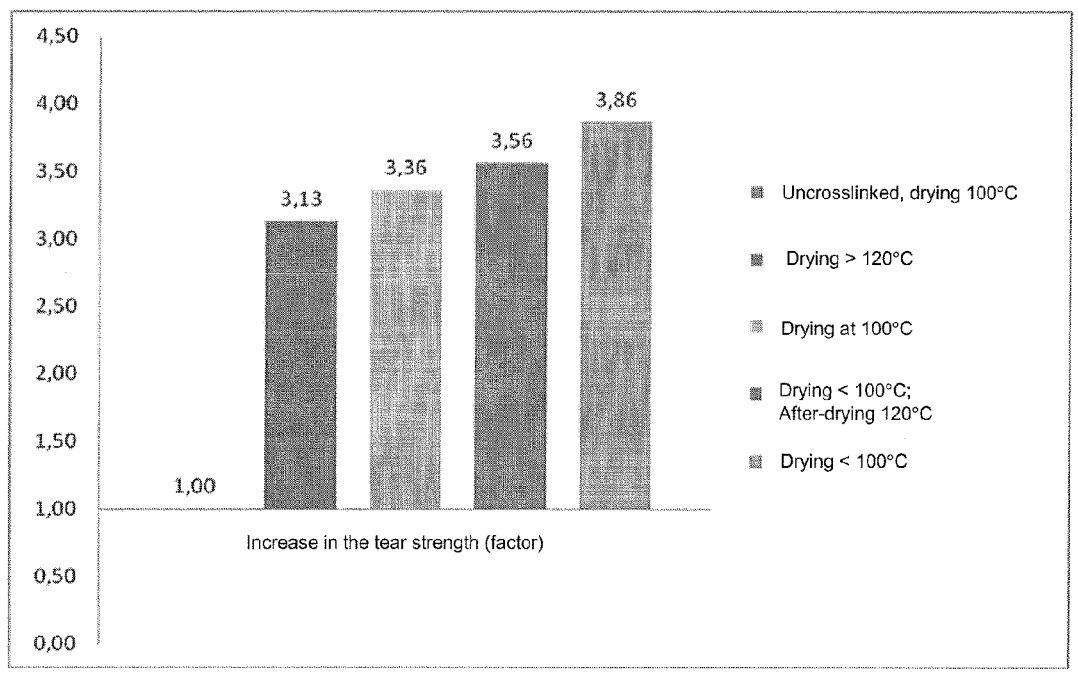

Test Results:

By way of example, FIG. 5 shows the improvement in the wet tear strength (according to internal method UV8801) of epoxy-crosslinked collagen matrices having a composition according to Preparation example 1a as compared with merely dehydrothermally crosslinked collagen matrices (uncrosslinked, drying 100° C., "uncrosslinked" denoting solely dehydrothermally crosslinked (i.e. not chemically crosslinked)).

FIG. 5 also shows the influence of the freeze-drying temperature on the wet tear strength. According to the figure, matrices exposed to a freeze-drying temperature ≥100° C. or to post-drying at >100° C. exhibit poorer wet tear strengths than the materials prepared according to the invention.

Figure 6:
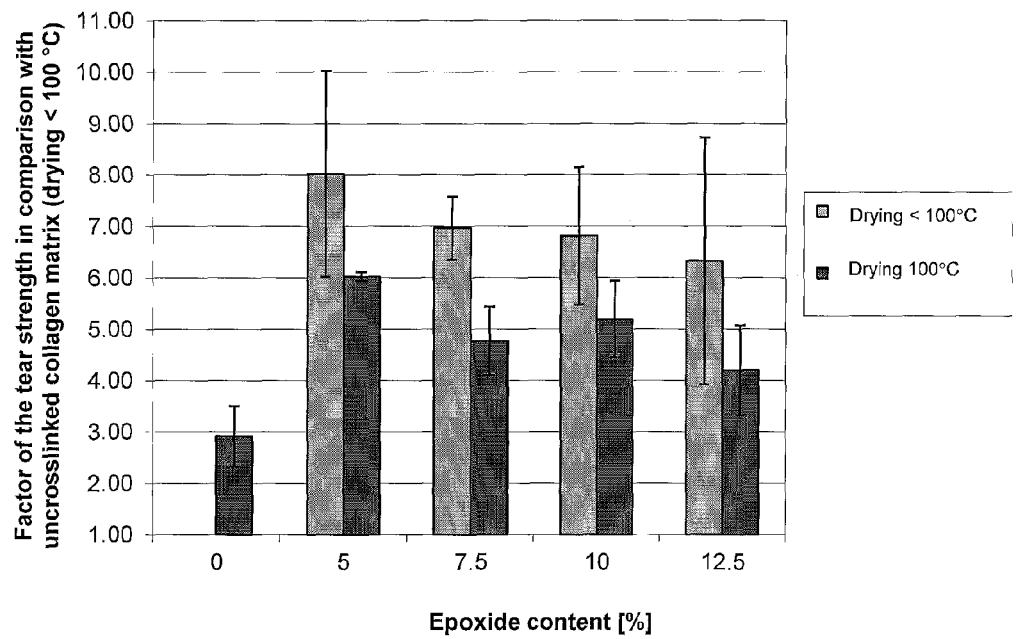

Moreover, FIG. 6 additionally shows the influence of the epoxide crosslinking agent concentration on the wet tear strength. It is shown that, as the epoxide concentration increases >5% (in DM of the aqueous collagen suspension/mixture), the wet tear strength decreases. Optimum wet tear strengths are achieved under the given process conditions with epoxide concentrations of from 5% to 10% (DM). The figure additionally shows, as expected, the increase in the wet tear strength of merely dehydrothermally crosslinked collagen materials as the freeze-drying temperature increases.

Figure 7:
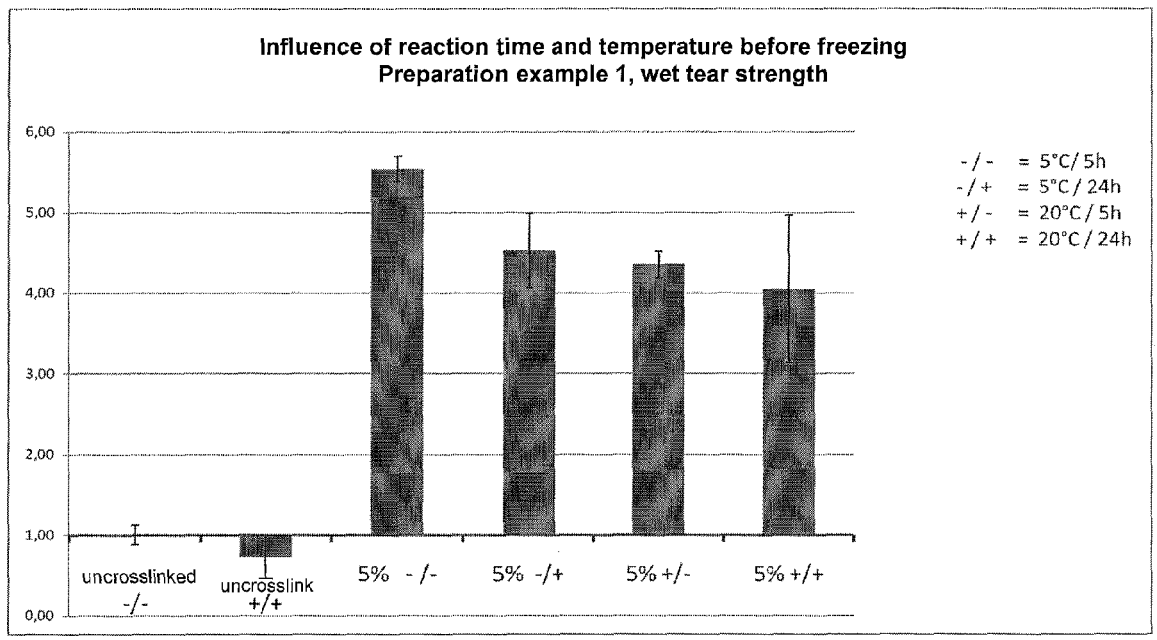

FIG. 7 shows the influence on the wet tear strength of the standing times and the temperature of the aqueous collagen suspension/mixture maintained thereby prior to freezing. It is clear therefrom that both longer standing times and higher temperatures adversely affect the wet tear strength of the collagen materials.

All the tested epoxy-crosslinked matrix materials exhibited wet tear strengths of >400 cN/mm layer thickness.

The dehydrothermally crosslinked material exhibited a wet tear strength of <200 cN/mm layer thickness.

Example 9

Detection of Reactive Epoxy Compounds
Determination of the Residual Epoxy Activity (NBP Assay)

The residual epoxy activity can be determined by means of a modified NBP assay (nitrobenzyl-pyridine assay) based on "Detection of Epoxides with 4-(p-nitrobenzylpyridine" by Agarwal et al. (1979) Bull. Environm. Contam. Toxicol. 23, p. 825-829, modified according to Zocher et al. (2000) "Epoxide hydrolase activity of *Streptomyces* strains" J. Biotechnol. February 17; 77(2-3), p. 287-292.

1. Principle

The test process is used for the quantitative determination of soluble, reactive epoxy compounds in the freeze-dried end product in the case of biomatrices stabilised with epoxides.

p-Nitrobenzylpyridine reacts with alkylating compounds (including epoxides) to give a colourless, sparingly soluble salt which, on reaction with a base, is deprotonated to a blue, sparingly soluble dye. The colour intensity can be detected by spectrometry at a wavelength of 570 nm.

2. Reagents/Chemicals para-Nitrobenzylpyridine (NBP) (Merck, for synthesis)
Ethylene glycol (Fluka, purum)
Acetone (Fluka, for UV spectroscopy)
Triethylamine (Fluka, purum)
1,4-Butanediol diglycidyl ether or BDDG or epoxide (Sigma Aldrich, purum)
RO water
prepared therefrom:
Substrate solution: Dissolve 1 g of NBP in 5 ml of ethylene glycol and 1.25 ml of acetone at 50° C.
(sufficient for 10 samples)
Base solution: 50% triethylamine in acetone (v/v)
(sufficient for 10 samples)

3. Devices

Test tube with ground glass, ground-glass stopper, ground-glass clamp or 50 ml laboratory flask with screw top
Hot cabinet and heating block (50° C.)
2 ml reaction vessels with safety closure or screw closure
Micropipettes for 200 µl and 1000 µl (Eppendorf), matching pipette tips UV spectrometer (570 nm)
1.5 ml disposable plastic cuvettes (Plastikbrand, No. 7591 50)

4. Specimens

Cutting (12 mm) of the collagen material to be tested, per specimen (in triplicate) 1-3 dies Comparison specimen: freeze-dried biomatrix without chemical crosslinker (e.g. merely dehydrothermally crosslinked collagen matrix)

5. Procedure

Substrate Solution:

For in each case 10 specimens, 1 g of NBP is weighed into a test tube with ground glass and mixed with 5 ml of ethylene glycol and 1.25 ml of acetone. For a higher number of specimens, multiply the amount accordingly and use a screw-top flask.

After carefully closing the vessel (ground-glass stopper/ground-glass clamp or screw top), the substrate mixture is heated in a hot cabinet at about 50° C. while occasionally being moved from side to side, until the solid has dissolved completely (½-1 hour). The substrate solution is then cooled to room temperature. The salt remains dissolved.

Base Solution:

Seal 3 ml of triethylamine and 3 ml of acetone in the test tube with ground glass and mix.

Preparation of the Standard Specimens for Calibration Curve:

Predilution:

1 g of epoxide, accurate to 0.001 g, is weighed directly into a 100 ml measuring flask by means of a Pasteur pipette (glass), made up to 100 ml with RO water and mixed thoroughly (1:100).

Exactly 1000 µl of the predilution are transferred by means of the 1000 µl pipette to a 100 ml measuring flask, made up to 100 ml and mixed thoroughly. This is the epoxide dilution (1:10,000) for generating the standard measured values (calibration curve).

Standard Measured Values:

Add equal amounts of 12 mm pieces of the comparison material (without crosslinker) to 2 ml reaction vessels, label the reaction vessels. Using the 200 µl pipette, add different volumes of RO water to the nonwoven (for volumes see row A, Table 1), then add 600 µl of substrate solution.

TABLE 1

Standard measured values

| | | Amount of epoxide (nmol) | | | |
|---|---|---|---|---|---|
| | | 0 | 12.5 | 25 | 50 | 75 |
| A | Volumes of RO water (μl) | 200 | 175 | 150 | 100 | 50 |
| B | Volumes of epoxide dilution (μl) | 0 | 25 | 50 | 100 | 150 |

Finally—only after the test specimens have been completed—add the epoxide dilution 1:10,000 (for volumes see row B, Table 1) to the standard series in the reaction vessel. Briefly move from side to side again.

Test Material:

1-3 12 mm pieces of the material to be tested are weighed, accurate to 0.1 mg, into 2 ml reaction vessels, in triplicate, and soaked with 200 μl of RO water. Then 600 μl of substrate solution are added to the soaked pieces.

Gently tap the reaction vessels until the suspension, which is initially cloudy, becomes clear. If the reaction solution is beneath the top, move the liquid back into the bottom by brief centrifugation. Incubate all the specimens, carefully sealed, for 1 hour at 50° C. in the hot cabinet or in the heating block.

Cool to room temperature, then add 600 μl of the base solution and shake briefly.

Measurement of the absorption must be carried out within 10 minutes.

Remove all the supernatant of the collagen pieces using the 1000 μl pipette and transfer to a 1.5 ml plastic cuvette.

Measure the absorption at 570 nm within 10 minutes after addition of the base solution.

Measuring programme: Methods/Concentration/ENBP

Calibration point: standard measured value 50 (=25 nmol epoxide)

Parallel beam and blank: empty plastic cuvette

6. Evaluation

The amount of reactive epoxide is determined by means of the calibration curves (relation concentration/absorption). The result of the measurement is related to the original weighed amount of the tested matrix material and gives:

Content of epoxide:ng/mg collagen

Figure 8:
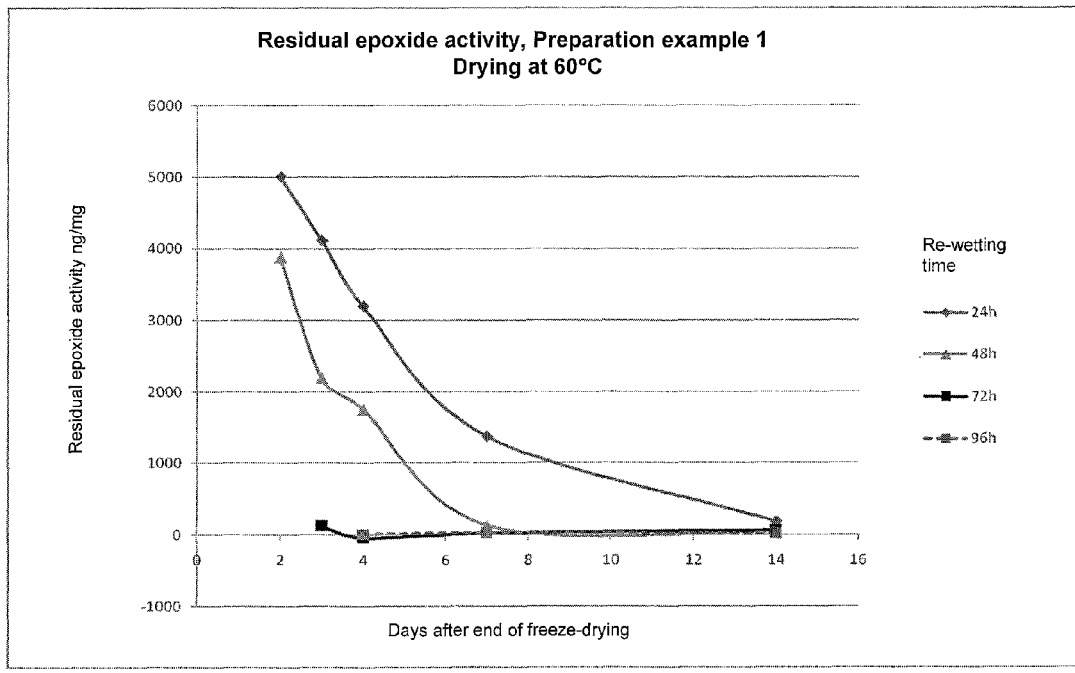

Test Results:

By way of example, FIG. 8 shows the residual epoxide activity of the collagen materials prepared according to the invention on the basis of a matrix according to Preparation example 1a and the exponential decrease thereof over time after freeze-drying (degradation curve). The matrices tested therein were dried at a freeze-drying temperature not exceeding 60° C. The figure additionally shows in particular the influence of re-hydration conditions on the reduction in the residual epoxide activity. For the test, the collagen materials were subjected to re-hydration under controlled climatic conditions, immediately after freeze-drying. The reduction in the residual activity of materials with a re-hydration period of a) 24 hours,
b) 48 hours,
c) 72 hours and
d) 96 hours was compared.

The determination was in each case carried out immediately after completion of re-hydration. Only sample a) was stored for 24 hours under normal ambient conditions before the first measurement was carried out. There are thus obtained the indicated measuring points after 48 hours (2 days) for specimens a) and b), 72 hours (3 days) for specimens a), b) and c), after 96 hours (4 days) for specimens a), b), c) and d) and after 168 hours (7 days) and after 336 hours (14 days) for all of specimens a) to d).

It is clear that the residual epoxide activity can be depleted markedly more quickly and reduced to a level that is no longer detectable as the re-hydration period increases.

Example 10

In Vitro Cytotoxicity Test (XTT Test) on Epoxy-Crosslinked Collagen Material According to Preparation Example 3

1. Equipment and Method 1.1 Test Material:

Freeze-dried epoxy-crosslinked collagen material according to Preparation example 3.

1.2. Preparation of the Extracts

From the test material, pieces of identical size (9.6 cm$^2$) were cut out of 3 different collagen sheets. The cut-out pieces were extracted for 24 hours at 37±1.5° C., with shaking, in 9.6 ml of cell culture medium (RPMI 1640 medium) supplemented with 10% FCS (Gibco, Invitrogen, Ref. No. 10270-106), 1 mM sodium pyruvate, 4 mN L-glutamine and 100 μg/ml penicillin/streptomycin (complete medium). Positive and negative controls were extracted in the same manner.

The test materials were extracted according to ISO 10993-12 at a surface area/volume ratio of 3 cm$^2$/ml.

1.3. Controls

Larger amounts of the extracts of the negative and positive controls were prepared beforehand and stored at −20° C. 100% extracts were thawed and diluted immediately before the treatment. The negative and positive controls were extracted in the complete medium according to ISO 10993-12 at a surface area/volume ratio of 6 cm$^2$/ml.

1.3.1 Negative Control

RM-C (High-Density Polyethylene)

Manufacturer: Hatano Research Institute, Hatano/Japan

Lot: C-042

1.3.2 Positive Control

Name.Latex

Supplier: VWR International GmbH (64295 Darmstadt, Germany)

Lot: 03200694110385

1.4 Test System 1.4.1 Criteria for Selection of Cell Line L929

The ATCC, CCL 1 NCTC clone 929 cell line (clone of strain L, mouse connective tissue) has successfully been used for many years in in vitro experiments. In particular the high proliferation rate (doubling time: 16 hours, measured on 22 Oct. 1992) and the good viability of untreated cells (generally more than 70%), both of which are necessary for suitable execution of the study, were aspects in favour of the choice of this cell line.

1.4.2 Cell Cultures

Large amounts of the L929 cell line (supplied by LMP, Technische Universitat Darmstadt, D-64287 Darmstadt) were stored in liquid nitrogen in the Harlan Cytotest Cell Research GmbH cell bank, which permits the repeated use of the same cell culture batch in the experiments. As a result, owing to the reproducible characteristics of the cells, it is ensured that constant parameters are maintained in the experiments.

Thawed stem cell cultures were multiplied at 37±1.5° C. in plastic bottles (Greiner, D-72634 Frickenhausen), cultivation was carried out with about 2×10$^5$ cells/culture bottle in 6 ml of complete medium. The cells were subcultivated twice weekly. The cell cultures were incubated at 37±1.5° C. and in a 5.0±0.5% carbon dioxide atmosphere.

1.5 Test Groups
1.5.1. Medium Control: Complete Medium
1.5.2. Negative Control: RM-C
extracted with complete medium for 24 hours, 100% extract
1.5.3. Positive Control: Latex
extracted with complete medium for 24 hours; 3% extract, 10% extract, 30% extract, 70% extract, 100% extract
1.5.4. Test Material: Collagen Matrix According to Preparation Example 3
extracted with complete medium for 24 hours; 3% extract, 10% extract, 30% extract, 100% extract
1.6 Test Procedure
1.6.1. Cell Cultivation Exponentially growing stem cultures, more than 50% confluent, were rinsed with Ca—Mg-free salt solution and treated with trypsin at 37±1° C. for 5 minutes (Gibco BRL trypsin/EDTA solution 10× Cat. No. 35400-019). Then the enzymatic dissolution was stopped by addition of the complete medium and a single cell suspension was prepared.

The Ca—Mg-free salt solution had the following composition (per liter):

| | |
|---|---|
| NaCl | 8000 mg |
| KCl | 400 mg |
| Glucose | 1000 mg |
| NaHCO$_3$ | 350 mg |

0.1 ml of medium containing about 15,000 cells was added to individual wells of a 96-well cell culture microtitre plate (Greiner). The medium was complete medium.

The plates were incubated for 24 hours in order to permit cell adhesion.

1.6.2 Treatment

The medium was then removed, and 0.1 molar treatment medium was added to the cells, the treatment medium containing different concentrations of the extracts of the test materials, of the negative and positive control extracts and of the medium control.

All incubations were carried out at 37±1.5° C. in a humid atmosphere in a 5.0±0.5% CO$_2$ atmosphere.

1.6.3 XTT Labelling and Measurement

After the incubation time of 24 hours, 50 μl of the XTT labelling mixture were added. The mixture contains the XTT labelling reagent and an electron coupling reagent (volume ratio 1:100). The cells were incubated for about 1 hour 35 minutes and then transferred to the microplate reader (Versamax® Molecular Devices, D-85737 Ismaning) equipped with a 450 nm filter for measurement of the absorption (reference wavelength 690 nm).

1.7 Data Recording

The data generated were recorded as raw data. The results are shown in the form of tables containing the test groups with the test materials, negative medium and control group.

1.8 Evaluation of the Results

A decrease in the number of living cells results in a decrease in the total activity of the mitochondrial dehydrogenase in the samples. This decrease correlates directly with the amount of orange formazan formed, measured by the absorption. The results for the dose-dependent cytotoxicity response can be shown as the arithmetic mean±standard deviation. In order to calculate the concentration of the toxic material that is necessary to reduce the absorption by 50% relative to the medium control (XTT$_{50}$), the following formula was used:

$$XTT_{50} = Conc._{>50} \frac{(Conc._{>50} - Conc._{<50}) \cdot (\%_{>50} - 50)}{(\%_{>50} - \%_{<50})}$$

a) Conc. >50=max. measured concentration with % of the medium control >50%
b) Conc. <50=min. measured concentration with % of the medium control <50%
c) %>50=relative absorption at a) in %
d) %<50=relative absorption at b) in %

The smaller the XTT$_{50}$ value, the higher the cytotoxic potential of the test material.

A reduction in the viability to <70% and ≥50% of the medium control means low cytotoxicity. In the case of a reduction in the viability to <50% of the medium control, cytotoxic potential is present.

2. Results 2.1. TABLE OF RESULTS
Results after 24 hours extraction in complete medium

| Test group | Extract concentration [%] | Absorption* | Standard deviation | Chem. blank values | Absorption in % of the medium control** |
|---|---|---|---|---|---|
| Medium control | | 1.388 | 0.155 | 0.101 | 100.00 |
| Test material | 3 | 1.246 | 0.141 | 0.101 | 88.97 |
| Test material | 10 | 1.283 | 0.057 | 0.102 | 91.76 |
| Test material | 30 | 1.258 | 0.046 | 0.103 | 89.74 |
| Test material | 100 | 1.320 | 0.028 | 0.100 | 94.79 |
| Negative control | 100 | 1.192 | 0.107 | 0.105 | 98.37 |
| Medium control | | 1.206 | 0.079 | 0.101 | 100.00 |
| Positive control | 3 | 1.273 | 0.144 | 0.105 | 105.70 |
| Positive control | 10 | 0.903 | 0.040 | 0.106 | 72.13 |
| Positive control | 30 | 0.130 | 0.002 | 0.109 | 1.90 |
| Positive control | 70 | 0.129 | 0.002 | 0.111 | 1.72 |
| Positive control | 100 | 0.134 | 0.001 | 0.114 | 1.81 |

Indicated absorptions show rounded-off values. Relative absorptions were calculated using the correct absorption values.
Shaded test groups represent test material concentrations at which microscopic investigations after the treatment show morphological changes in the cells due to the occurrence of cytotoxicity.
*mean absorption (absolute) of 7 wells
**relative absorption [rounded-off values]:

$$\frac{100 \times (absorbance_{specimen} - absorbance_{chem.blanks})}{(absorbance_{solvent\ control} - absorbance_{chem.blanks})}$$

XTT$_{50}$ values of the test materials could not be calculated because the viability of the cells was not reduced in a relevant manner.

XTT$_{50}$ values of the positive control: 16.3% (v/v)

3. Discussion

This in vitro study was carried out in order to investigate the cytotoxic potential of freeze-dried epoxy-crosslinked collagen material according to Preparation example 3 by means of the XTT test using the mouse cell line L929.

Identical test pieces (9.6 cm$^2$) were cut out of three test materials, and the cut pieces were extracted as described hereinbefore.

The following concentrations of test extracts were studied:
3%, 10%, 30% and 100% (v/v)
the following concentrations of extracts (positive control) were tested:
3%, 10%, 30%, 70% and 100% (v/v)

No relevant differences could be observed between the medium control (complete medium) and the negative control (extracted negative control RM-C).

The positive control (latex) exhibited a marked dose-dependent reduction in cell viability and cell proliferation. With the undiluted reference standard extract (100%), a reduction in the cell viability and/or cell proliferation in the respective wells of about 1.81% was found. The calculated XTT$_{50}$ value is 16.3% (v/v).

Cytotoxic effects after incubation could not be observed in any of the tested extracts of the collagen material according to Preparation example 3. The XTT$_{50}$ value could not be calculated because the viability of the cells was not reduced in a relevant manner.

4. Result

In summary, within the context of this test under the described experimental conditions, extracts of the test material according to Preparation example 3 did not demonstrate any cytotoxic potential at all up to the highest test concentration.

Example 11

Measurement of the Rigidity/Modulus of Elasticity E (According to Stok et al.; J Biomed Mater Res; 2009) of Epoxy-Crosslinked Collagen Material According to Preparation Examples 2a and 2b (5% and 10% Epoxide Crosslinking Agent/Dry Mass)

The rigidity was measured according to Stok et al. 2009 by compression tests using a material testing machine (Zwick/Roell 1456, Ulm) with a 5 N force sensor. A suitable size for the test die was calculated according to Spilker et al.; Journal of Biomechanical Engineering, series 114, H. 2, p. 191-201; 1992; the diameter was 1.38 mm. The specimen was located in a holder on a micro coordinate table (see fig.), where it was covered with a layer of PBS. A plexiglass cover prevented the sample from bending upwards.

The die was moved into the specimen stepwise to a depth of 5%, 15% and 25% of the speicmen thickness and held until the system had relaxed. The modulus of elasticity was determined from the mean of the last ten values of the equilibrium phase of three impression steps:

Modulus of elasticity [kPa] is the gradient of the strain (x) and stress (y)

Strain=depth of penetration [mm]/thickness of the specimen [mm]

Stress=force [mN]/surface area of the die [mm$^2$]

The specimen was immersed in PBS for at least 15 minutes, placed into the holder and left there, covered with a layer of PBS, for at least 5 minutes. The surface of the sample was defined as the position at which the sensor detected 0.1 mN resistance. Determination of the E values was carried out by measurement in triplicate (n=3).

Figure 9:
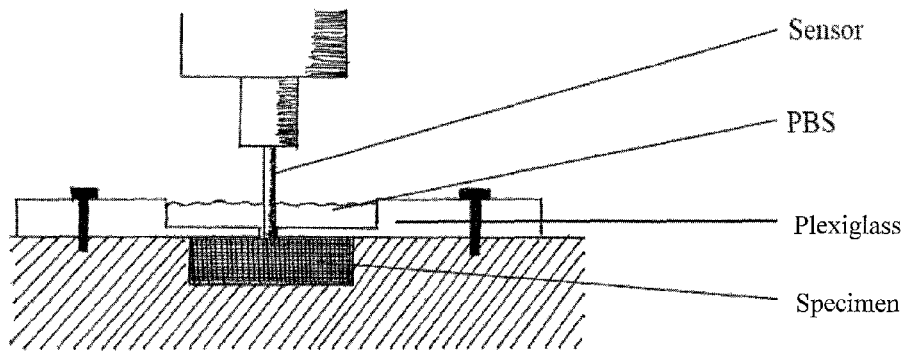

The test arrangement is shown by way of example in FIG. 9.

Result:

Collagen matrices according to Preparation example 2a (5% epoxide) exhibit a rigidity of 9 kPa.

Collagen matrices according to Preparation example 2b (10% epoxide) exhibit a rigidity of 22 kPa.

An uncrosslinked collagen-elastin matrix (dehydrothermally crosslinked) exhibited a rigidity of only 6 kPa.

Example 12

Use of the Crosslinked Collagen Matrices

The materials according to the invention of Preparation examples 1 to 3 are particularly suitable for use as a cosmetic and pharmaceutical agent.

Application Example 12a

Use as a Cosmetic Mask

For treatment, the materials according to the invention of Preparation examples 1 to 3 are cut to the desired shape and size of the area of skin to be treated and either
a) placed in the dry state on the skin to be treated and rehydrated by wetting with water or an activator solution until saturated, or
b) soaked with water or an activator solution until saturated before being placed on the skin, and then placed in the rehydrated state on the area of skin to be treated.

The rehydrated collagen dressings were left on the treated areas of skin for a period of approximately from 20 to 30 minutes.

During this treatment there was a marked lessening of existing redness or irritation, as well as of existing itching, a fresher appearance, greater skin elasticity and improved skin hydration.

Application Example 12b

Use as a Subcutaneous Implant

The materials according to the invention of Preparation examples 1 and 2 can be used as a subcutaneous implant in the field of plastic or reconstructive surgery with the aim of reconstructive volume building, for example, in cases of skin volume loss secondary to various causes in the region of the midface, for rhinoplasty procedures as well as for aesthetic reconstructive operations, required, for instance, after tumour surgery or following trauma independent of the body part involved.

Before implantation, the material, in the dry state, can be cut and correspondingly adapted to the underlying area of skin.

Before the matrix is introduced into the prepared skin pocket, it must be rehydrated in large quantities of sterile physiological saline or Ringer's solution. Insertion of the matrix into the prepared subdermal skin pocket is carried out rapidly immediately after rehydration of the matrix in sterile physiological saline or Ringer's solution is completed. Wound closure is to be adapted according to the operative procedure and is to be decided by the treating doctor.

Action of the Matrix:

On implantation, the matrix acts as a scaffold and allows the ingrowth of cells which are involved in building skin tissue.

The migrated cells synthesise autologous tissue structures during the healing process and so provide for the desired increase in volume in the region of the inserted implant.

As tissue neogenesis progresses, the structure of the matrix can be completely resorbed and remodelled.

The native structurally intact collagen template is optimally suited for promoting the in-growth of cells and vessels; this consequently supports the regeneration of tissue. The use of the matrix placed between two different tissue layers acts prophylactically against adhesion formation and secondary contractures.

Application Example 12c

Use as Dermis Replacement (Implant) (Acute and Chronic Wounds)

The materials according to the invention of Preparation examples 1 and 2 can be used for dermis construction in combination with autologous split-skin transplants in the case of deep dermal defects and full-thickness skin wounds in burns surgery, in plastic-reconstructive surgery and in the treatment of poorly healing wounds (e.g. chronic wounds) requiring a transplant.

Application:

The corresponding piece of material is removed sterile from the packaging and roughly cut to fit the skin defect.

The dry material is then placed on the wound and first pressed into the wound area by means of a stomach cloth.

The material gets soaked with wound fluids and adheres to the wound ground without the risk of formation of air pockets. The edges are cut into a circle leaving a narrow overlap of about 2 mm.

If the material is seated properly in the wound area, saline solution is carefully applied by means of a syringe; alternatively, a very wet stomach cloth soaked with saline solution can be applied and left for a few minutes. After this time, the material is completely rehydrated and is located exactly in the wound bed according to the previous placing.

Transplantation of the split skin into the wound area is carried out directly on the material. Additional securing of the material together with the split skin is achieved by stitching or staples. If the matrix is not covered with the split-skin transplant until a later time, it should be ensured that it does not dry out. A sterile, non-adherent gauze soaked with physiological saline solution is suitable for this purpose.

For covering the wound, it is recommended to use a non-occlusive silicone foil or several layers of active-ingredient-free fatty gauze in order to ensure a moist wound environment. Hitherto, it has been found to be advantageous in practice to use a tight bandage of a combination of 5-6 layers of fatty gauze and 3-4 layers of gauze bandage. The bandaging technique should be designed to ensure good contact between the split skin, the matrix and the wound base and to absorb shear forces. The application of a vacuum bandage to treated wounds is governed by the doctor's decision in each particular case. In many cases, good results have been achieved with this bandaging technique.

The aim of the treatment is to construct a neodermis, in order to improve the quality of the restored skin. Scarring is to be reduced and wound contraction is to be prevented.

Application Example 12d

Use as a Haemostatic Agent (Acute and Surgical Wounds)

The materials according to the invention of Preparation examples 1 and 2 can be used as a haemostatic agent for local administration, preferably in the case of operations with venous and diffuse bleeding, for example in visceral surgery, cardiothoracic vascular surgery, neurosurgery, maxillary surgery and general stomatology, ENT, urology and gynaecology.

The material is preferably placed in the dry state on the swabbed wound and modelled slightly thereto, but it can also be wetted before use. In the case of more severe bleeding, tamponading can be carried out with a wet compress. Larger wound areas are provided with several pieces; for small areas, the material can be appropriately cut with scissors.

Mode of Action:

The material absorbs several times its own weight of liquid. The thrombocytes aggregate at the large inner surface and contribute to local haemostasis by release of clotting factor. The fibrin that forms anchors the collagen matrix to the wound base and thus forms a stable wound closure.

Rapid haemostasis can be achieved by this treatment.

Application Example 12e

Use as a Dermal/Transdermal Wound Dressing for Exuding Wounds (Chronic Wounds)

The materials according to the invention of Preparation examples 1 and 2 can be used as a wound dressing for local interactive wound treatment. For optimal action, the material should be applied directly to the entire wound bed. In wounds with no or slight exudation, the material can be rehydrated with saline or Ringer's solution.

The wound dressing must be covered with a suitable secondary bandage in order to maintain a moist wound healing environment. After the first application, the wounds should be treated with the material again at intervals of up to 72 hours, depending on the extent of the exudate. Any non-resorbed matrix can remain in the wound.

Mode of Action:

The material is able to absorb several times its own weight in liquid and is therefore excellently suitable for the management of the wound liquid. With the absorption of the wound secretion, necroses, bacteria and fibrin coverings ejected by the wound can also be absorbed, as a result of which the formation of the granulation tissue can be aided and accelerated. Both effects contribute towards accelerating wound healing.

Application Example 12f

Use in Vacuum-Assisted Wound Treatment Therapy (Chronic Wounds)

For use, the materials according to the invention of Preparation examples 1 and 2 are applied in the dry state to the body parts to be treated or to the wound, the material being cut to the shape of the wound if necessary. The material is then thoroughly soaked and rehydrated either by the wound fluids present or with water or an aqueous solution or physiological saline solution. It is additionally possible to wet the materials according to the invention before they are applied to the body part to be treated.

The wound is then closed in an air-tight manner with a conventional vacuum-tight covering foil. After application of a suitable vacuum, the wound liquid is drawn off by conventional vacuum therapy processes by means of conventional devices for conveying away the wound fluid (drainage unit).

By means of this treatment it is possible to achieve a reduction in the wound surface area, a contraction of the wound edges, an enhancement of the formation of granulation tissue and, in addition, an acceleration of wound healing.

EXPLANATIONS OF THE FIGURES

FIG. 1: BCA method: Determination of the soluble protein constituents [%] in an epoxy-crosslinked collagen matrix with additional soluble matrix proteins (elastin hydrolysate) according to Preparation example 2 in comparison with a solely dehydrothermally crosslinked collagen matrix with elastin hydrolysate ("uncrosslinked").

FIG. 2a: Collagenase digestion test: Determination of the degradation rate [%] of epoxy-crosslinked collagen matrices according to the invention of Preparation examples 1a and 2a in comparison with a solely dehydrothermally crosslinked collagen matrix with elastin hydrolysate ("uncrosslinked"); within a period of 6 hours.

FIG. 2b: Collagenase digestion test: Determination of the absolute amount of the dissolved portion of epoxy-crosslinked collagen matrices according to the invention (normalised to 10 mg) of Preparation examples 1a and 2a in comparison with a solely dehydrothermally crosslinked collagen matrix with elastin hydrolysate ("uncrosslinked"); within a period of 23 hours.

FIG. 3: Hydrolytic stability: a) dehydrothermally crosslinked collagen matrix ("uncrosslinked") with triglycerides/neutral oil (freeze-drying temperature >120° C.); b) epoxy-crosslinked collagen matrix according to the invention of Preparation example 3 (5% epoxide/DM; with triglycerides/neutral oil; freeze-drying temperature <100° C.); c) epoxy-crosslinked collagen matrix corresponding to the composition according to Preparation example 3 (5% epoxide/DM; with triglycerides/neutral oil; freeze-drying temperature >120° C.).

FIG. 4: Degree of hydrolysis after 18 days a) of a dehydrothermally crosslinked collagen matrix in comparison with b) a collagen matrix according to the invention of Preparation example 3.

FIG. 5: Influence of the freeze-drying temperature on the wet tear strength (internal method UV8801).

FIG. 6: Influence of the freeze-drying temperature and of the epoxide crosslinker concentration on the wet tear strength (internal method UV8801).

FIG. 7: Influence of the standing time and of the temperature during the standing time of the aqueous collagen suspension/mixture before freezing on the wet tear strength (internal method UV8801).

FIG. 8: Residual epoxide activity and influence of re-wetting on the reduction in the residual epoxide activity of a collagen matrix according to the invention of Preparation example 1.

FIG. 9: Test arrangement for measuring the rigidity/modulus of elasticity E.

The invention claimed is:
1. A crosslinked collagen matrix obtained by a process comprising:
   a) preparing an aqueous collagen suspension,
   b) adjusting the pH value of the collagen suspension from step a) to pH <4,
   c) adding an epoxy-functional crosslinking agent in an amount of not more than 50 wt. % based on the dry mass of the collagen suspension from step a),
   d) freezing the collagen mixture obtainable from step d),
   e) freeze-drying of the frozen mixture from step e) at a freeze-drying temperature <100° C.,
   f) adjusting the freeze-dried crosslinked collagen material so obtained to a moisture content from 3 to 25 wt. %, based on the end product, and
   g) at least one of sterilizing and processing the formed materials.

2. The crosslinked collagen matrix of claim 1, wherein the collagen suspension from step a) comprises native acid-insoluble collagen in the form of fibers and fibrils.

3. The crosslinked collagen matrix of claim 1, wherein the collagen suspension comprises acid-soluble collagen and peptide constituents and/or wherein in step c) structure-forming agents or active ingredients from the group of the matrix proteins, extracellular matrix constituents, proteinogenic active ingredients and soluble protein or peptide constituents are added.

4. The crosslinked collagen matrix of claim 1, having a wet tear strength >50 cN/mm layer thickness, measured by DIN EN ISO 3376, or >200 cN/mm layer thickness, measured by the UV8801 method.

5. The crosslinked collagen matrix according to claim 1, having a collagenase degradation rate, characterized by an amount of decomposition products after collagenase digestion in phosphate-buffered saline after 6 hours, determined by means of an UVNIS spectral photometer, of not more than 85%.

6. The crosslinked collagen matrix according to claim 1, having a hydrolytic stability of greater than or equal to 90%, determined by the formula Hydrolytic stability (%)=$M_{tx} \times 100/M_{t0}$ with $M_{tx}$=mass of the dried intact/cohesive collagen matrix material $M_{t0}$=mass of the dry collagen matrix material before the start of the test, within 18 days of storing the crosslinked collagen matrix in an aqueous solution, consisting of water, glycerol, 1,5-pentanediol, sodium chloride and a preservative, at 50° C.

7. The crosslinked collagen matrix according to claim 1, having a rigidity, corresponding to a modulus of elasticity according to the Young's modulus E, of 0.01 to 100 kPa.

8. The crosslinked collagen matrix according to claim 1, having a liquid absorption capacity of 1 to 200 times its own weight.

9. The crosslinked collagen matrix of claim 1, wherein the epoxy-functional crosslinking agent is a diepoxide.

10. The crosslinked collagen matrix of claim 9, wherein the diepoxide is 1,4-butanediol diglycidyl ether.

11. The crosslinked collagen matrix of claim 1, wherein the process from which it is obtained further comprises converting the materials obtainable from step g) into a desired form to afford formed materials.

12. The crosslinked collagen matrix of claim 1, wherein the process from which it is obtained further comprises adding at least one of structure-forming agents, active ingredients and auxiliary substances.

13. The crosslinked collagen matrix of claim 12, wherein the at least one active ingredient is selected from the group consisting of dermal and transdermal active ingredients: for skin treatment, for the treatment of skin diseases, for wound treatment or for hemostasis, antibacterial wound treatment agents.

* * * * *